United States Patent [19]

Schlee et al.

[11] 4,056,527
[45] Nov. 1, 1977

[54] TETRAHYDRO-1,3,5-TRIAZINE-2,6-DIONES

[75] Inventors: Hans Georg Schlee, Cologne; Klaus Sasse, Schildgen; Ludwig Eue, Cologne, all of Germany

[73] Assignee: Bayer Aktiengesellschaft, Leverkusen, Germany

[21] Appl. No.: 407,693

[22] Filed: Oct. 18, 1973

[30] Foreign Application Priority Data

Nov. 6, 1972 Germany .......................... 2254200

[51] Int. Cl.² .................. C07D 251/16; C07D 251/42; A01N 9/22
[52] U.S. Cl. ......................... 544/194; 71/93; 544/211; 544/223; 544/218
[58] Field of Search .................. 260/248 NS, 249.5

[56] References Cited

U.S. PATENT DOCUMENTS

| | | | |
|---|---|---|---|
| 3,835,133 | 9/1974 | Seckinger | 260/248 |
| 3,855,219 | 12/1974 | Fuchs et al. | 260/248 |
| 3,873,540 | 3/1975 | Fuchs et al. | 260/248 |
| 3,933,815 | 1/1976 | Ploeg | 260/248 |
| 3,983,116 | 9/1976 | Lin | 260/249.5 |

OTHER PUBLICATIONS

Schaefer et al., *Journal of the American Chemical Soc.*, vol. 73, pp. 2996–2999 (1951).

*Primary Examiner*—John M. Ford
*Attorney, Agent, or Firm*—Burgess, Dinklage & Sprung

[57] ABSTRACT

New tetrahydro-1,3,5-triazine-2,6-dione compounds of the formula

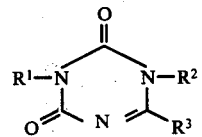

(I)

in which
$R^1$ is optionally substituted aliphatic or aromatic hydrocarbyl,
$R^2$ is hydrogen, alkyl, cycloalkyl, aralkyl, aryl, hydroxy, alkoxy, acyloxy, or $-NR^4R^5$,
$R^4$ and $R^5$ are individually hydrogen, alkyl or acyl, optionally substituted with nitrile, hydroxyl and/or halogen, or
$R^4$ and $R^5$ together represent alkylidene, and
$R^3$ is hydrogen, alkyl, halogenoalkyl, halogen, aryloxy or an $-NR^6R^7$ radical wherein $R^6$ and $R^7$ individually are selected from hydrogen, alkyl, cycloalkyl, aralkyl, aryl, hydroxyl, amino or alkoxy and $R^6$ and $R^7$ together with the nitrogen atom, represent a heterocyclic radical;
$R^3$, with the proviso that $R^2$ is other than hydrogen, can also be alkoxy or alkylmercapto.

19 Claims, No Drawings

TETRAHYDRO-1,3,5-TRIAZINE-2,6-DIONES

The present invention relates to certain new tetrahydro-b 1,3,5-triazine-2,6-dione compounds, to herbicidal compositions containing them, and their use as herbicides.

It is known that hexahydro-1,3,5-triazine-2,4,6-triones display a certain herbicidal action from German Offenlegungsschrift (German Published Specification ) No. 1,927,921. However, the activity of these materials is not always satisfactory.

The present invention provides, as new compounds, the tetrahydro-1,3,5-triazine-2,6-diones of the general formula

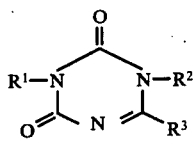

in which
R¹ is saturated or unsaturated, aliphatic or cycloaliphatic hydrocarbyl, araliphatic hydrocarbyl or aryl, each of which can carry one or more substituents selected from halogen, nitro, alkyl, alkoxy, alkylmercapto, aryl, aryloxy, halogenomethyl or arylmercapto,
R² is hydrogen, alkyl, cycloalkyl, aralkyl, aryl, hydroxy, alkoxy, acyloxy, or

wherein
R⁴ and R⁵, which may be identical or different, are each hydrogen, alkyl or acyl, i.e., alkanoyl, (the alkyl and acyl radicals are optionally substituted by nitrile and/or hydroxyl and/or halogen), or
R⁴ and R⁵ together represent alkylidene (which can carry one or more substituents selected from aryl, halogenoaryl, alkoxyaryl, nitroaryl and heterocyclic radicals), or cycloalkylidene, and
R³ is hydrogen, alkyl, halogenoalkyl, halogen, aryloxy or an

radical wherein R⁶ and R⁷ individually are selected from hydrogen, alkyl, cycloalkyl, aralkyl, aryl, hydroxyl, amino or alkoxy and R⁶ and R⁷ together with the nitrogen atom, represent a heterocyclic radical;
R³, with the proviso that R² is other than hydrogen, can also be alkoxy or alkylmercapto.

The compounds of this invention have been found to display strong herbicidal properties.

Preferably, R¹ is straight-chain or branched alkyl of from 1 to 12 carbon atoms, which may be substituted by halogen, or cycloalkyl of from 5 to 7 carbon atoms, aralkyl or aryl radical which may be substituted by halogen, alkyl or trifluoromethyl; R² is hydrogen, alkyl of from 1 to 4 carbon atoms, cycloalkyl of from 5 to 7 carbon atoms, aralkyl, aryl or an

radical, wherein R⁴ and R⁵ are each hydrogen, alkyl or acyl, or R⁴ and R⁵ conjointly form alkylidene (which may optionally be carrying one or more substituents selected from aryl, halogenoaryl, alkoxyaryl, nitroaryl and heterocyclic radicals) or cycloalkylidene; and R³ is straight-chain or branched alkyl of from 1-10 carbon atoms, alkoxy, alkylmercapto or an

radical, wherein R⁶ and R⁷ are hydrogen, alkyl, hydroxyl, amine or alkoxy.

This invention also provides processes for the production of a tetrahydro-1,3,5-triazine-2,6-dione of the formula (I) in which
a. a bis-(chlorocarbonyl)-amine for the general formula

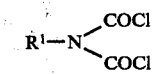

in which
R¹ has the above-mentioned meaning, is reacted with a compound of the general formula

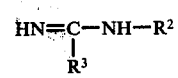

in which
R² and R³ have the above-mentioned meaning, or a salt thereof with an organic or inorganic acid, in the presence of acid-binding agents, it being possible, when R² is hydroxyl or amino, to protect this group by acylation or hydrazone formation and to liberate it again after the reaction,
or (b) a compound of the general formula

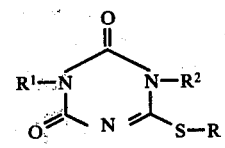

in which
R¹ and R² have the above-mentioned meanings, and
R is an alkyl radical which is optionally substituted, for example by carboxyl,
is reacted with a compound of the general formula

in which
R⁶ and R⁷ have the above-mentioned meanings,
or (c) a compound of the general formula

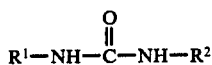

in which

R¹ and R² have the above-mentioned meanings, is reacted with chlorocarbonylisocyanide dichloride of the formula

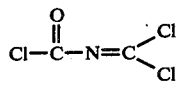

optionally in the presence of acid-binding agents, to give a compound of the general formula

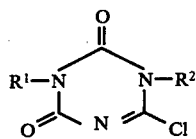

in which

R¹ and R² have the above-mentioned meanings, and this compound is optionally reacted with a compound of the formula R³—H, in the presence of an acid-binding agent, or with a compound of the formula R³—M, in which M is an alkali metal atom or a magnesium halide moiety and R³ in each case has the above-mentioned meaning, or (d) a compound of the general formula

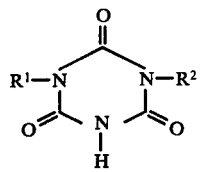

in which

R¹ and R² have the above-mentioned meanings, is reacted with an inorganic acid halide to give a compound of the general formula (VIII) above, which is then optionally reacted with a compound of the formula R³—H, in the presence of an acid-binding agent, or with a compound of the formula R³—M as defined above.

Surprisingly, thetetrahydro-1,3,5-triazine-2,6-diones according to the invention display a substantially greater herbicidal activity than the hexahydro-1,3,5-triazine-2,4,6-triones known from the state of the art. The compounds according to the invention thus represent an enrichment of the art.

If, in accordance with process variant (a), N-phenyl-bis (chlorocarbonyl)-amine and acetone-S-methyl iso-thiosemicarbazone hydroiodide are used in the presence of triethylamine, and the splitting reaction is subsequently carried out in a weakly acid solution, the course of the reaction can be represented by the following equation:

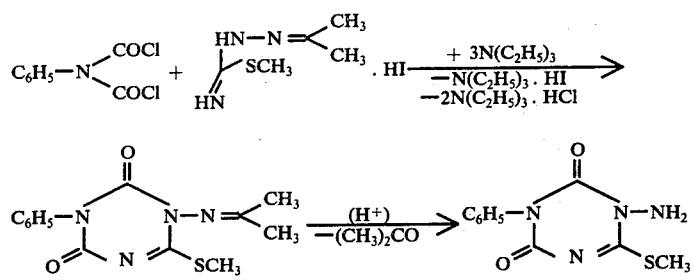

If, according to process variant (b), 1-isopropyl-3-amino-4-methylmercapto-tetrahydro-1,3,5-triazine-2,6-dione and ethylamine are used in the presence of p-toluenesulphonic acid as the catalyst, the course of the reaction can be represented by the following equation:

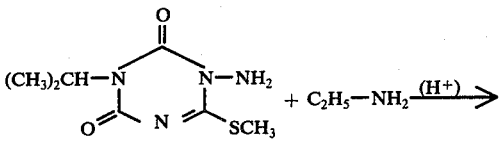

If, according to process variant (c), N-(4-chlorophenyl)-N'-ethylurea, chlorocarbonylisocyanide dichloride and sodium thiomethylate are used or if, according to process variant (d), 1-(4-chlorophenyl)-3-ethyl-hexahydro-1,3,5-triazine-2,4,6-trione, phosphorus pentachloride and sodium thiomethylate are used, the course of the reactions can be represented by the following equation:

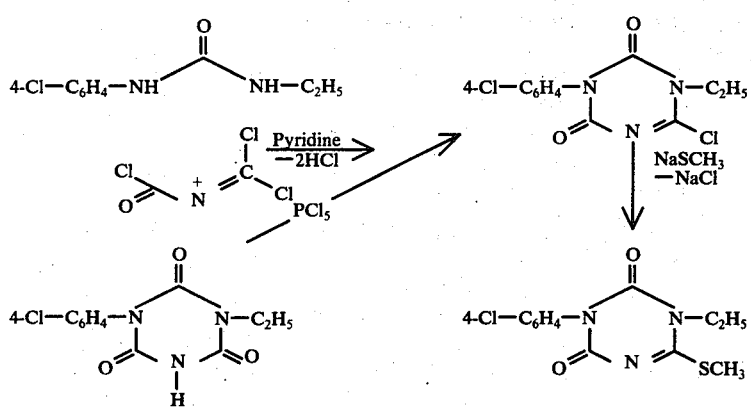

The bis-(chlorocarbonyl)-amines (II) which can be used according to the invention are in part already known (see Synthesis 1970, page 542-543); the compounds which have not yet been described in the literature can be produced analogously. The following may be mentioned as examples: N-methyl-(bis-chlorocarbonyl)-amine, N-ethyl-(bis-chlorocarbonyl)-amine, N-propyl-(bis-chlorocarbonyl)-amine, N-isopropyl-(bis-chlorocarbonyl)-amine, N-sec.-butyl-(bis-chlorocarbonyl)-amine, N-tert.-butyl-(bis-chlorocarbonyl)-amine, N-octyl-(bis-chlorocarbonyl)-amine, N-dodecyl-(bis-chlorocarbonyl)-amine, N-cyclopropyl-(bis-chlorocarbonyl)-amine N-cyclohexyl-(bis-chlorocarbonyl)-amine, N-cycloocytl-(bis-chlorocarbonyl)-amine, N-benzyl-(bis-chlorocarbonyl)-amine N-(4-chlorobenzyl)-(bis-chlorocarbonyl)-amine, N-(4-methylbenzyl)-(bis-chlorocarbonyl)-amine, N-phenyl-(bis-chlorocarbonyl)-amine, N-(4-methylphenyl)-(bis-chlorocarbonyl)-amine, N-(4-ethylphenyl)-(bis-chlorocarbonyl)-amine, N-(3-chlorophenyl)-(bis-chlorocarbonyl)-amine, N-(4-chlorophenyl)-(bis-chlorocarbonyl)-amine, N-(3,4-dichlorophenyl)-(bis-chlorocarbonyl)-amine, N-(2,4-dichlorophenyl)-(bis-chlorocarbonyl)-amine, N-(4-bromophenyl)-(bis-chlorocarbonyl)-amine, N-(3-nitrophenyl)-(bis-chlorocarbonyl)-amine, N-(4-methoxyphenyl)-(bis-chlorocarbonyl)-amine, N-(4-methoxy-3-chlorophenyl)-(bis-chlorocarbonyl)-amine, N-(3-triflouromethyl-phenyl)-(bis-chlorocarbonyl)-amine and N-(2-chloro-5-trifluoromethylphenyl)-(bis-chlorocarbonyl)-amine.

The compounds of the formula (III) which can be used according to the invention are already extensively known; those that have not yet been described in the literature can be produced according to known processes (see, for example, Houben-Weyl, Methoden der organischen Chemie (Methods of Organic Chemistry), 4th edition, volume VIII, pages 170-193, volume IX, pages 884-915 and volume XI/2, pages 38-69). The following may be mentioned as examples: formamidine hydrochloride, acetamidine hydrochloride, isobutyramidine hydrochloride, butylamidine hydrochloride, O-acetyl-acetamidoxime, O-acetylpropionamidoxime, S-methyl-isothiourea sulphate, N,S-dimethyl-isothiourea hydroiodide, N-ethyl-S-methyl-isothiourea hydriodide, N-butyl-S-ethyl-isothiourea hydroiodide, N-benzyl-S-methyl-isothiourea hydroiodide, N-cyclohexyl-S-methyl-isothiourea hydroiodide, N-phenyl-S-ethylisothiourea hydroiodide, N-(4-chlorophenyl)-S-methyl-isothiourea hydroiodide, acetone-S-methyl-isothiosemicarbazone hydroiodide, methyl ethyl ketone-S-ethyl-isothiosemicarbazone hydroiodide, acetaldehyde-S-methyl-isothiosemicarbazone hydroiodide, propionaldehyde-S-methyl-isothiosemicarbazone hydroiodide, phenylacetaldehyde-S-methyl-isothiosemicarbazone hydroiodide, cyclohexanone-S-methyl-isothiosemicarbazone hydroiodide, 4-chlorobenzaldehyde-S-methyl-isothiosemicarbazone hydroiodide, 3,4-dichlorobenzaldehyde-S-methyl-isothiosemicarbazone hydroiodide, 3-nitrobenzaldehyde-S-methylisothiosemicarbazone hydroiodide, 4-methoxybenzaldehyde-S-methyl-isothiosemicarbazone hydroiodide, furfuraldehyde-S-methyl-isothiosemicarbazone hydroiodide, 1-isopropylideneacetamidrazone, 1-isopropylidene-propionamidrazone and 1-methyl-S-methyl-isothiosemicarbazide hydroiodide.

The 4-alkyl-mercapto-tetrahydro-1,3,5-triazine-2,6-diones (IV) which can be used according to the invention have not previously been described in the literature; howevwer, they can be produced according to process variant (a). The following may be mentioned as examples: 1-methyl-3-amine-4-methylmercapto-tetrahydro-1,3,5-triazine-2,6-dione, 1-ethyl-3-amine-4-methylmercapto-tetrahydro-1,3,5-triazine-2,6-dione, 1-isopropyl-3-amino-4-methylmercapto-tetrahydro-1,3,5-triazine-2,6-dione, 1-tert.-butyl-3-amino-4-methylmercapto-tetrahydro-1,3,5-triazine-2,6-dione, 1-cyclohexyl-3-amino-4-methylmercapto-tetrahydro-1,3,5-triazine-2,6-dione, 1-benzyl-3-amino-4-methylmercapto-tetrahydro-1,3,5-triazine-2,6-dione, 1-phenyl-3-amino-4-methylmercapto-tetrahydro-1,3,5-triazine-2,6-dione, 1-(3,4-dichlorophenyl)-3-amino-4-methylmercapto-tetrahydro-1,3,5-triazine-2,6-dione, 1-methyl-4-methylmercapto-tetrahydro-1,3,5-triazine-2,6-dione, 1-isopropyl-4-methylmercapto-tetrahydro-1,3,5-triazine-2,6-dione, 1-tert.-butyl-4-methylmercapto-tetrahydro-1,3,5-triazine-2,6-dione, 1-cyclohexyl-4-methylmercapto-tetrahydro-1,3,5-triazine-2,6-dione, 1-benzyl-4-methylmercapto-tetrahydro-1,3,5-triazine-2,6-dione, 1-phenyl-4-methylmercapto-tetrahydro-1,3,5-triazine-2,6-dione, 1-(3,4-dichlorophenyl)-4-methylmercapto-tetrahydro-1,3,5-triazine-2,6-dione, 1-isopropyl-3-methyl-4-methylmercapto-tetrahydro-1,3,5-triazine-2,6-dione, 1-tert.-butyl-3-methyl-4-methylmercapto-tetrahydro-1,3,5-triazine-2-6-dione,1-cyclohexyl-3-methyl-4-methyl mercapto-tetrahydro-1,3,5-triazine-2,6-dione, 1-phenyl-3-methyl-4-methylmercapto-tetrahydro-1,3,5-triazine-2,6-dione, 1-isopropyl-3-ethyl-4-methylmercapto-tetrahydro-1,3,5-triazine-2,6-dione, 1-tert.-butyl-3-ethyl-4-methylmercapto-tetrahydro-1,3,5-triazine-2,6-dione, 1-cyclohexyl-3-ethyl-4-methylmercapto-tetrahydro- 1,3,5-triazine-2,6-dione, 1-phenyl-3- ethyl-4-methylmercapto-tetrahydro-1,3,5-triazine-2,6-dione, 1,3,-diisopropyl-4-methylmercapto-tetrahydro-1,3,5-triazine-2,6-dione, 1-tert.-butyl-3-iospropyl-4-methylmercapto-tetrahydro-1,3,5-triazine-2,6-dione, 1-cyclohexyl-3-isopropyl-4-methylmercapto-tetrahydro-1,3,5-triazine-2,6-dione, 1-phenyl-3-isopropyl-4-methylmercapto-tetrahydro-1,3,5-triazine-2,6-dione, 1-isopropyl-3-methylamino-4-methylmercapto-tetrahydro-1,3,5-triazine-2,6-dione, 1-tert.-butyl-3-methylamino-4-methylmercapto-tetrahydro-1,3,5-triazine-2,6-dione, 1-cyclohexyl-3-methylamino-4-methylmercapto-tetrahydro-1,3,5-triazine-2,6-dione, 1-phenyl-3-methylamino-4-methylmercapto-tetrahydro-1,3,5-triazine-2,6-dione, 1-isopropyl-3-hydroxy-4-methylmercapto-tetrahydro-1,3,5-triazine-2,6-dione, 1-tert.-butyl-31 hydroxy-4-methylmercapto-tetrahydro-1,3,5-triazine-2,6-dione, 1-cyclohexyl-3-hydroxy-4-methylmercapto-tetrahydro-1,3,5-triazine-2,6-dione, 1-phenyl-3-hydroxy-4-methylmercapto-tetrahydro-1,3,5-triazine-2,6-dione, 1- isopropyl-3-amino-4-carboxymethylmercapto-tetrahydro-1,3,5-triazine-2,6-dione and 1-isopropyl-3-ethyl-4-carboxymethylmercapto-tetrahydro-1,3,5-triazine-2,6-dione.

The compounds of the formula (V) used as starting materials in process variant (b) are already known. As examples there may be mentioned: ammonia, methylamine, dimethylamine, ethylamine, isopropylamine, butylamine, diethylamine, benzylamine, hydrazine, hydroxylamine, O-methylhydroxylamine and N,O—dimethylhydroxylamine.

The compounds of the formula (VI), employed as starting materials in process variant (c), are already extensively known; the compounds that have not previously been described in the literature can be prepared according to known processes. As examples there may be mentioned: N,N'-dimethyl-urea, N-methyl-N'-isopropyl-urea, N-methyl-N'-tert.-butyl-urea, N-methyl-N']benzyl-urea, N-methyl-N'-cyclohexyl-urea, N-methyl-N'-phenyl-urea, N,N'-diethyl-urea, N-ethyl-N'-iso-propyl-urea, N-ethyl-N'-tert.-butyl-urea, N-ethyl-N'-benzyl-urea, N-ethyl-N'-cyclohexyl-urea, N-ethyl-N'-phenyl -urea, N,N'-diisopropyl-urea, N-methoxy-N'-isopropyl-urea, 1-isopropylidene-4-methyl-semicarbazone, 1-isopropylidene-4-isopropyl-semicarbazone, 1-isoisopropylidene-4-tert.-butyl-semicarbazone, 1-isopropylidene-4-cyclohexyl-semicarbazone, 1-isopropylidene-4-phenyl-semicarbazone, 1-benzylidene-4-methyl-semicarbazone, 1-benzylidene-4-isopropyl-semicarbazone, 1-benzylidene-4-tert.-butyl-semicarbazone, 1-benzylidene-4-cyclohexyl-semicarbazone, 1-benzylidene-4-phenyl-semicarbazone, 1-cyclohexylidene-4-methyl-semicarbazone, 1-cyclohexylidene-4-isopropyl-semicarbazone, 1-cyclohexylidene-4-tert.-butyl-semicarbazone, 1-cyclohexylidene-4-cyclohexyl-semicarbazone, 1-cyclohexylidene-4-phenyl-semicarbazone, 1-methyamino-4-methyl-semicarbazide, 1-methylamino-4-isopropyl-semicarbazide, 1-methylamino-4-tert.-butyl-semicarbazide, 1-methylamino-4-cyclohexyl-semicarbazide and 1-methylamino-4-phenyl-semicarbazide.

Chlorocarbonylsulphenyl chloride, which is used as a starting material in process variant (c), is already known from German Patent Specification No. 1,244,720.

The compounds $R^3$—H or $R^3$—M employed in process variants (c) and (d), and in which M is preferably Li, Na, K, MgCl, MgBr or MgI, are already known. As examples there may be mentioned: methyllithium, methyl-magnesium bromide, ethylamine, ethyllithium, butyl-lithium, sodium methylate, sodium ehtylate, sodium thiomethylate, sodium thioethylate, ammonia, methylamine, propylamine, isopropylamine, dimethylamine, diethylamine, hydrazine, methyl-hydrazine, 1,1-dimethylhydrazine, hydroxylamine, O-methyl-hydroxylamine and N,O-dimethyl-hydroxylamine.

The compounds of the formula (IX) which can be used according to process variant (d) are already largely known; the compounds that have not yet been described in the literature can be prepared according to known processes. As examples there may be mentioned: 1-methyl-3-isopropylideneamino-hexahydro-1,3,5-triazine-2,4,6-trione, 1-isopropyl-3-isopropylideneamino-hexahydro-1,3,5-triazine-2,4,6-trione, 1-tert.-butyl-3-isopropylideneamino-hexahydro-1,3,5-triazine-2,4,6-trione, 1-cyclohexyl-3-isopropylideneamino-hexahydro-1, 3,5-triazine -2,4,6-trione, 1-benzyl-3-isopropylideneamino-hexahydro-1,3,5-triazine-2,4,6-trione, 1-phenyl-3-isopropylideneamino-hexahydro-1,3,5-triazine-2,4,6-trione, 1-(3,4-dichlorophenyl)-3-isopropylideneamino-hexahydro-1,3,5-triazine-2,4,6-trione, 1-isopropyl-3-methyl-hexahydro-1,3,5-triazine-2,4,6-trione, 1-tert.-butyl-3-methyl-hexahydro-1,3,5-triazine-2,4,6-trione, 1-cyclohexyl-3-methyl-hexahydro-1,3,5-triazine-2,4,6-trione, 1-phenyl-3-methyl-hexahydro-1,3,5-triazine-2,4,6-trione, lisopropyl-3-ethyl-hexahydro-1,3,5-triazine-2,4,6-trione, 1-tert.-butyl-3-ethyl-hexahydro-1,3,5-triazine-2,4,6-trione, 1-cyclohexyl-3-ethyl-hexahydro-1,3,5-triazine-2,4,6-tione, 1-phenyl-3ethyl-hexahydro-1,3,5-triazine-2,4,6-trione, 1-isopropyl-3-isopropyl-hexahydro-1,3,5-triazine-2,4,6-trione, 1-tert.-butyl-3-isopropyl-hexahydro-1,3,5-triazine-2,4,6-trione, 1-cyclohexyl-3-isopropyl-hexahydro-1,3,5-triazine-2,4,6-trione, 1-phenyl-3-isopropyl-hexahydro-1, 3,5-triazine-2,4,6-trione, 1-isopropyl-3-methylamino-hexahydro-1,3,5-triazine-2,4,6-trione, 1-tert.butyl-3-methylamino-hexahydro-1,3,5-triazine-2,4,6-trione, 1-cyclohexyl-3-methylamino-hexahydro-1,3,5-triazine-2,4,6-trione and 1-phenyl-3-methylamino-hexahydro-1,3,5-triazine-2,4,6-trione.

Amongst the inorganic acid halides which can be used in process variant (d), thionyl chloride, phosgene, phosphorus oxychloride or phosphorus pentachloride are preferred.

Possible diluents for process (a) are all inert organic solvents, especially hydrocarbons, such as petroleum ether, benzene, tolune and xylene; ethers, such as diethyl ether, diisopropyl ether and dioxane; and acid amides, such as dimethylformamide and dimethylacetamide.

All customary acid-binders can be used as acid-binding agents: the alkali metal hydroxides, alkali metal carbonates, alcoholates and tertiary amines are preferred. Particularly suitable are sodium hydroxide, potassium hydroxide, sodium carbonate, potassium carbonate, potassium tert.-butylate, pyridine, triethylamine, triethylenediamine, diemthylaniline and diisopropyl ethylamine.

The reaction temperatures can be varied over a fairly wide range. In general, the reaction is carried out between 0° and 50° C, preferably between 20° and 40° C.

In carrying out the process variant (a), 1 mole of the compound (III) is generally employed per mole of bis-chlorocarbonylamine (II), and 2-4 moles of acid-binder are generally added to neutralize the acid produced. The reaction takes place exothermically. The resulting salts are removed by filtration or by extraction by shaking with water, the organic phase is evaporated and the residue is recrystallized.

Any desired organic solvents can be used as diluents in process variant (b). Preferred solvents are alcohols, such isopropanol or tert.-butanol; carboxylic acids, such as formic acid and glacial acetic acid; and ethers, such as diethyl ether or dioxane.

Any desirable inorganic and organic acids can be added as catalysts; however, the oxygen acids of phosphorus, carboxylic acids, sulphonic acids, or mixtures thereof are preferred. Phosphoric acid, glacial acetic acid, trichloroacetic acid, benzenesulphonic acid and p-toluenesulphonic acid may be mentioned as being particularly suitable.

The reaction temperatures can be varied over a fairly wide range. In general, the reaction is carried out between 0° and 50° C, preferably between 20° and 30 ° C.

In carrying out the process variant (b), an excess of 5–10 moles of the compound (V) is generally employed per mole of the compound (IV).

The amount of the catalyst added can vary from 0.1 mole to 1 mole of the compound (IV).

Depending on the nature of the compound (V), the latter is introduced in the gaseous form into the prepared reaction solution or is added dropwise to the prepared reaction solution. The reaction takes place slightly exothermically, with elimination of mercaptan. After completion of the elimination, the reaction mixture is concentrated in vacuo and the residue is purified by crystallization.

Possible diluents for process (c) are all inert organic solvents, especially hydrocarbons, such as benzine, benzene or toluene, and ethers, such as diethyl ether and dioxane.

Possible acid-binders are all non-nucleophillic acid-binding agents, preferably tertiary amines. Particularly suitable are triethylamine, diisopropylethylamine, triethylenediamine, pyridine and dimethylaniline.

The reaction temperatures can be varied over a fairly wide range. In general, the reaction is carried out between −20° and 40° C, preferably between 0° And 30 ° C.

In carrying out process variant (c), 1 mole of chlorocarbonylisocyanide dichloride (VII) is employed per 1mole of a compound according to the formula (VI), and the resulting acid is bound by twice the molar amount of a suitable acid acceptor. The reaction takes place exothermically.

The resulting salts are removed by filtration and the reaction solution is further reacted with 1 mole of a compound of the formula $R^3$—H in the presence of 1 mole of an acid-binder or with 1 mole of a compound of the formula $R^3$—M. The salts are removed by filtration or by extraction by shaking with water, the organic phase is concentrated in vacuo and the residue is recrystallized. However, the intermediate compound (VIII) can also be isolated.

Possible diluents in process (d) are all inert organic solvents, especially hydrocarbons, such as benzine, benzene and toluene, and chlorinated hydrocarbons, such as methylene chloride, chloroform and carbon tetrachloride.

The reaction temperatures can be varied over a fairly wide range. In general, the reaction is carried out at between 20° and 120° C, preferably between 40° and 80° C.

In carrying out process variant (d), 1-10 moles of the inorganic acid halide, which is either introduced in the gaseous form or added in portions, are generally employed per 1 mole of the compound (IX). The reaction takes place with evolution of gas. At the end of the reaction time, excess acid halide or its reaction products are removed by applying a vacuum. The intermediate stage (VIII) which is formed can then be reacted further, with or without isolation, as described above for process variant (C).

The reaction in process variants (a), (b), (c) and (d) are preferably carried out under normal pressure but if volatile reactants are used they can also be carried out under elevated pressure, The following may be mentioned as examples of the new active compounds (I): 1-methyl-3-ethyl-4-methylmercapto-tetrahydro-1,3,5-triazine-2,6-dione, 1-methyl-3-isopropylideneamino-4-methylmercapto-tetrahydro-1,3,5-triazine-2,6-dione, 1-methyl-3-amino-4-methyamino-tetrahydro-1,3,5-triazine-2, 6-dione, 1-methyl-3-amino-4-ethyl-tetrahydro-1,3,5-triazine-2,6-dione, 1-ethyl-3-amino-4-methylmercapto-tetrahydro-1,3,5-triazine-2,6-dione, 1-ethyl-3-hydroxy-4-ethyl-tetrahydro- 1,3,5-triazine-2,6-dione, 1-isopropyl-4-methyl-tetrahydro-1,3,5-triazine-2,6-dione, 1-isopropyl-4-ethyl-tetrahydro-1,3,5-triazine-2,6-dione, 1-isopropyl-4-methylamino-tetrahydro-1,3,5-triazine-2,6-dione, 1-isopropyl-4-dimethylamino-tetrahydro-1,3,5-triazine-2,6-dione, 1-isopropyl-4-ethylamino-tetrahydro-1,3,5-triazine-2,6-dione, 1-isopropyl-3-amino-4-methyl-tetrahydro-1,3,5triazine-2,6-dione, 1-isopropyl-3-amino-4-ethyl-tetrahydro-1,3,5-triazine-2,6-dione, 1-isopropyl-3-amino-4-methylmercapto-tetrahydro-1,3,5-triazine-2,6-dione, 1-isopropyl-3-amino-4-methylamino-tetrahydro-1,3,5-triazine-2,6-dione, 1-isopropyl-3-amino-4-dimethylamino-tetrahydro-1,3,5-triazine-2,6-dione, 1-isopropyl-3-amino-4-ethylamino-tetrahydro-1,3,5-triazine-2,6-dione. 1-isopropyl-3-amino-4-hydroxylamino-tetrahydro-1,3,5triazine-2,6-dione, 1-isopropyl-3-amino-4-hydrazino-tetrahydro-1,3,5-triazine-2,6-dione, 1-isopropyl-3-ethylideneamino-4-methylmercapto-tetrahydro-1,3,5-triazine-2,6-dione, 1-isopropyl-3-isopropylidemeamino-4-methylmercapto-tetrahydro-1,3,5-triazine-2,6-dione, 1-isopropyl-3-cyclohexylideneamino-4-methymercapto-tetrahydro-1,3,5-triazine-2,6 dione, 1-isopropyl-3-benzylideneamino-4-methylmercapto-tetrahydro-1,3,5-triazine-2,6-dione, 1-isopropyl-3-ethylideneamino-4-methylamino-tetrahydro-1,3,5-triazine-2,6-dione, 1-isopropyl-3-isopropylideneamino-4-ethlamino-tetrahydro-1,3,5-triazine-2,6-dione, 1-isopropyl-3-cyclohexylideneamino-4-hydroxylamino-tetrahydro-1,3,5-triazine-2,6-dione, 1-isopropyl-3-benzylideneamino-4-hydrazion-tetrahydro-1,3,5-triazine-2,6-dione, 1-isopropyl-3-hydroxy-4-methyl-tetrahydro-1,3,5-triazine-2,6-dione, 1-isopropyl- 3-methoxy-4-ethyl-tetrahydro-1,3,5-triazine-2,6-dione, 1-isopropyl-3-hydroxy-4-methylmercapto-tetrahydro-1,3,5-triazine-2,6-dione, 1-isopropyl-3-hydroxy-4-methylamino-tetrahydro-1,3,5-triazine-2,6-dione, 1-isopropyl-3-hydroxy-4-ethylamino-tetrahydro-1,3,5-triazine-2,6-dione, 1-isopropyl-3-hydroxy-4-hydroxylamino-tetrahydro-1,3,5-triazine-2,6-dione, 1-isopropyl-3-methylamino-4-methyl-tetrahydro-1,3,5-triazine-2,6-dione, 1-isopropyl-3-methylamino-4-ethyl-tetrahydro-1,3,5-triazine-2,6-dione, 1-isopropyl-3-methylamino-4-methylmercap-to-tetrahydro-1,3,5-triazine-2,6-dione, 1-isopropyl-3-methyl-amino-4-ethylamino-tetrahydro-1,3,5-triazine-2,6]dione, 1-isopropyl-3-methyl-4-methylmercapto-tetrahydro-1,3,5-triazine-2,6-dione, 1-isopropyl-3-ethyl-4-methylmercapto-tetrahydro-1,3,5-triazine-2,6-dione, 1-isopropyl-3-isopropyl-4-methylmercapto-tetrahydro-1,3,5-triazine-2,6-dione, 1-isopropyl-3-phenyl-4-methylmercapto-tetrahydro-1,3,5-triazine-2,6-dione, 1-isopropyl-3-methyl-4-methylamino-tetrahydro-1,3,5-triazine-2,6-dione, 1-isopropyl-3-methyl-4-dimethylamino-tetrahydro-1,3,5-triazine-2,6dione, 1-isopropyl-3-methyl-4-ethylamino-tetrahydro-1,3,5-triazine-2,6-dione, 1-isopropyl-3-ethyl-4-methylamino-tetrahydro-1,3,5-triazine-2,6-dione, 1-isopropyl-3-ethyl-4ethylamino-tetrahydro-1,3,5-triazine-2,6dione, 1-isopropyl-3-ethyl-4-dimethylamino-tetrahydro-1,3,5-triazine-2,6-dione, 1-isopropyl-3-isopropyl-4-methylamino-tetrahydro-1,3,5-triazine-2,6-dione, 1-isopropyl-3-isopropyl-4-ethylamino-tetrahydro-1,3,5-triazine-2,6-dione, 1-isopropyl-3-benzyl-4-methylmercapto-tetrahydro-1,3,5-triazine-2,6-dione, 1-isopropyl-3-benzyl-4-methylamino-tetrahydro-1,3,5-triazine-2,6-dione, 1-isopropyl-3-methyl-4-methyl-tetrahydro-1,3,5-triazine-2,6-dione, 1-isopropyl-3-methyl-4-ethyl-tetrahydro-1,3,5-triazine-2,6-dione, 1-isopropyl-3-benzyl-4-ethyl-tetrahydro-1,3,5-triazine-2,6-dione, 1-isopropyl-3-methyl-4-hydroxylamino-tetrahydro-1,3,5-triazine-2,6-dione, 1-isopropyl-3-ethyl-4-hydroxylamino-tetrahydro-1,3,5-triazine-2,6-dione, 1-isopropyl-3-benzyl-4-hydroxylamino-tetrahydro-1,3,-5-triazine--2,6-dione, 1-sec.-butyl-3-amino-4-methylmercapto-tetrahydro-1,3,5-triazine-2,6-dione, 1-sec.-butyl-3-benzylideneamino-4-ethyl-tetrahydro-1,3,5-triazine-2,6-dione, 1-tert.-butyl-3-amino-4-methylmercapto-tetrahydro-1,3,5-triazine-2,6-dione, 1-tert.-butyl-3-isopropylideneamino-4-methylmercapto-tetrahydro-1,3,5-triazine-2,6-dione, 1-tert.-butyl-3-amino-4-methylamino-tetrahydro-1,3,5-triazine-2,6-dione, 1-tert.-butyl-3-amino-4-ethylamino-tetrahydro-1,3,5-triazine-2,6-dione, 1-tert.-butyl-3-hydroxy-4-ethyl-tetrahydro-1,3,5-triazine-2,6-cione, 1-butyl-3-amino-4-methylmercapto-tetrahydro-1,3,5-triazine-2,6-dione, 1-octyl-3-amino-4-methylmercapto-tetrahydro-1,3,5-triazine-2,6-dione, 1-dodecyl-3-amino-4-methyl-mercapto-tetrahydro-1,3,5-triazine-2,6-dione, 1-cyclohexyl-3-amino-4-methylmercapto-tetrahydro-1,3,5-triazine-2,6-dione, 1-cyclohexyl-3-isobutylideneamino-4-methylamino-tetrahydro-1,3,5-triazine-2,6-dione, 1-cyclohexyl-3-amino-4-ethylaminotetrahydro-1,3,5-triazine-2,6-dione, 1-cyclohexyl-3-hydroxy-4-ethyl-tetrahydro-1,3,5-triazine-2,6-dione, 1-cyclohexyl-31ethyl-4-hydroxylamino-tetrahydro-1,3,5-triazine-2,6-dione, 1-benzyl-3-isopropylideneamino-4-methylmercapto-tetrahydro-1,3,5-triazine-2,6-dione, 1-benzyl-3-amino-4-ethyl-tetrahydro- 1,3,5-triazine-2,6-dione, 1-benzyl-3-amino-4-methylaminotetrahydro-1,3,5-triazine-2,6-dione, 1-benzyl-3-hydroxy-4-ethyl-tetrahydro-1,3,5-triazine-2,6-dione, 1-benzyl-3-ethyl-4-ethylamino-tetrahydro-1,3,5-triazine-2,6-dione, 1-phenyl-3-amino-4-ethyl-tetrahydro-1,3,5-triazine-2,6-dione, 1-phenyl-3-benzylideneamino-4-methylmercapto-tetrahydro-1,3,5-triazine-2,6-dione, 1-phenyl-3-amino-4-ethylamino-tetrahydro-1,3,5-triazine-2,6-dione, 1-phenyl-3-amino-4-hydrazino-tetrahydro-1,3,5-triazine-2,6-dione, 1-phenyl-3-ehtyl-4-hydroxylaminotetrahydro-1,3,5-triazine-2,6-dione,1-(4-chlorophenyl)-3-amino-4-methylmercapto-tetrahydro-1,3,5-triazine-2,6-dione, 1-(4-chlorophenyl)-3-amino-4-ethylamino-tetrahydro-1,3,5-triazine-2,6-dione, 1-(3,4-dichlorophenyl)-3-amino-4-methylmercapto-tetrahydro-1,3,5-triazine-2,6-dione, 1(3,4-dichlorophenyl)-3-ethyl-4-hydroxylamino-tetrahydro-1,3,5-triazine-2,6-dione, 1-(4-methylphenyl)-3-amino-4-methylmercapto-tetrahydro-1,3,5-triazine-2,6-dione, 1-(4-methylphenyl)-3-hydroxy-4-ethyl-tetrahydro-1,3,5-triazine-2,6-dione, 1-(4-methoxyphenyl)-3-amino-4-methylmercapto-tetrahydro-1,3,5-triazine-2,6-dione, 1-(4-methoxyphenyl)-3-amino-4-methylamino-tetrahydro-1,3,5-triazine-2,6-dione, 1-(3-trifluoromethylphenyl)-3-amino-4-methylmercapto-tetrahydro-1,3,5-triazine-2,6-dione, and 1-(3-trifluoromethylphenyl)-3-ethyl-4-ethylamino-tetrahydro-1,3,5-triazine-2,6-dione.

The preparation of the compounds of the present invention is illustrated in the following preparative examples:

EXAMPLE 1

Preparation of 1-methyl-3-isopropylideneamino4-methyl-mercapto-tetrahydro-1,3,5-triazine2,6-dione.

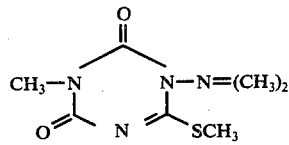

(Compound 1)

15.6 g (0.1 mole) of N-methyl-bis-(chlorocarbonyl)-amine were dissolved in 100 ml of benzene and added dropwise, whilst stirring, to 27.3 g (0.1 mole) of acetone-S-methyliso-thio-semicarbazone hydroiodide suspended in 100 ml of benzene. Thereafter, 30.3 g (0.3 mole) of triethylamine in 50 ml of benzene were slowly added dropwise. The mixture was stirred for a further hour and the precipitate was filtered off. The precipitate was introduced into 100 ml of chloroform and 100 ml of water and extracted by shaking. The chloroform phase was separated off, dried over calcium chloride and evaporated in vacuo, together with the benzene filtrate. The resudue was recrystallized from isopropanol. 17.3 g (76%) of 1-methyl-3-isopropylideneamino-4-methylmercapto-tetrahydro-1,3,5-triazine-2,6-dione were obtained as a colorless powder; melting point 130-132° C.

EXAMPLE 2

Preparation of 1-methyl-3-amino-4-methylmercaptotetrahydro-1,3,5-triazine-2,6-dione

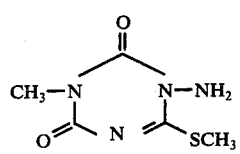

(Compound 2)

22.8 g (0.1 mole) of 1-methyl-3-isopropylideneamino-4-methylmercapto-tetrahydro-1,3,5-triazine-2,6-dione (prepared according to Example 1) were dissolved in 250 ml of ethanol and warmed, with addition of a pinch of p-toluene-sulphonic acid, for 5 hours to 50° C, whilst applying a vacuum of about 200 mm Hg. The mixture was evaporated in vacuo and the residue was recrystallized from ethanol. 18 g (96%) of 1-methyl3-amino-4-methylmercapto-1,3,5-triazine-2,6-dione were obtained as colorless needles; melting point 174°-175° C.

EXAMPLE 3

Preparation of 1-methyl-3-amino-4-methylaminotetrahydro-1,3,5-triazine-2,6-dione.

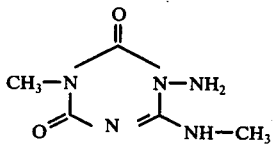

(Compound 3)

18.8 g (0.1 mole) of 1-methyl-3-amino-4-methylmercaptotetrahydro-1,3,5-triazine-2,6-dione (prepared according to Example 2) were idssolved in 200 ml of isopropanol with addition of 6 g of glacial acetic acid and a pinch of ptoluenesulphonic acid and the mixture was saturated with methylamine gas at room temperature. The batch was left to stand for about 10 hours and was evaporated in vacuo, and the resudue was recrystallized from isopropanol. 15 g (88%) of 1-methyl-3-amino-4-methylamino-tetrahydro-1,3,5-triazine2,6-dione were obtained as a colorless powder; melting point 225°–227° C.

EXAMPLE 4

Preparation of 1-isopropyl-3-isopropylideneamino-4-methylmercaptotetrahydro-1,3,5-triazine-2,6-dione.

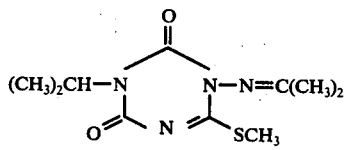

(Compound 4)

Analogously to Example 1, N-isopropyl-bis-(chlorocarbonyl)-amine (prepared analogously to Synthesis 1970, pages 542-543; boiling point 66-67° C/12 mm Hg) and acetone-S-methylisothio-semicarbazone hydroiodide, with addition of triethylamine, yielded 1-isopropyl-3-isopropylideneamino-4methylmercaptotetrahydro-1,3,5-triazine-2,6-dione as a pale yellow powder of melting point 110-112° C.

EXAMPLE 5

Preparation of 1-isopropyl-3-amino-4-methylmercaptotetrahydro-1,3,5-triazine-2,6-dione.

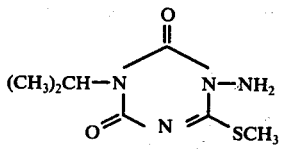

(Compound 5)

Analogously to Example 2, 1-isopropyl-3-isopropylideneamino-4-methylmercapto-tetrahydro-1,3,5-triazine-2,6-dione (prepared according to Example 4) yielded 1-isopropyl-3-amino4-methylmercapto-tetrahydro-1,3,5-triazine-2,6-dione as colorless needles of melting point 148°–150° C.

EXAMPLE 6

Preparation of 1-isopropyl-3-amino-4-methylamino-tetrahydro-1,3,5-triazine-2,6-dione.

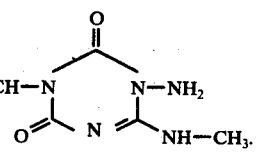

(Compound 6)

Analogously to Example 3, 1-isopropyl-3-amino-4-methylmercapto-tetrahydro-1,3,5-triazine-2,6-dione (prepared according to Example 5) and methylamine yielded 1-isopropyl-3-amino-4-methylamino-tetrahydro-1,3,5-triazine-2,6-dione as a colorless powder of melting point 195°–196° C.

EXAMPLE 7

Preparation of 1-isopropyl-3-amino-4-dimethylaminotetrahydro-1,3,5-triazine-2,6-dione.

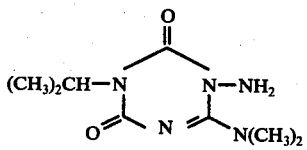

(Compound 7)

Analogously to Example 3, 1-isopropyl-3-amino-4-methylmercapto-tetrahydro-1,3,5-triazine-2,6-dione (prepared according to Example 5) and dimethylamine yielded 1-isopropyl-a-amino-4-dimethylamino-tetrahydro-1,3,5-triazine-2,6-dione as a colorless powder of melting point 131°–133° C.

EXAMPLE 8

Preparation of 1-isopropyl-3-amino-4-ethylaminotetrahydro-1,3,5-triazine-2,6-dione.

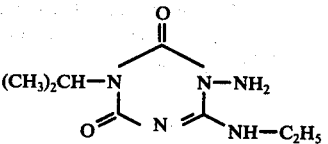

(Compound 8)

Analogously to Example 3, 1-isopropyl-3-amino-4-methylmercapto-tetrahydro-1,3,5-triazine-2,6-dione (prepared according to Example 5) and ethylamine yielded 1-isopropyl-3-amino-4-ethylamino-tetrahydro-1,3,5-triazine-2,6-dione as a colorless powder of melting point 122°–123° C.

EXAMPLE 9

Preparation of 1-cyclohexyl-3-isopropylideneamino4-methylmercapto-tetrahydro-1,3,5-triazine-2,6dione.

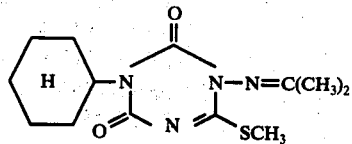

(Compound 9)

Analogously to Example 1, N-cyclohexyl-bis-(chloro-carbonyl)-amine (prepared analogously to Snythesis 1970, pages 542-543; boiling point 80°-82° C/0.3 mm Hg) and acetone-S-methylisothiosemicarbazone hydroiodide, with addition of triethylamine, yielded 1-cyclohexyl-3-isopropylideneamino-4-methylmercaptotetrahydro- 1,3,5-triazine-2,6-dione as a pale yellow powder of melting point 111°-112° C.

EXAMPLE 10

Preparaton of 1-cyclohexyl-3-amino-4-methylmercapto-tetrahydro-1,3,5-triazine-2,6-dione.

(Compound 10)

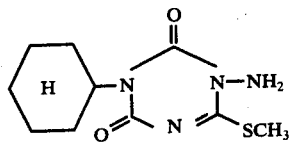

Analogously to Example 2, 1-cyclohexyl-3-isopropylideneamino-4-methylmercapto-tetrahydro-1,3,5-triazine-2,6-dione (prepared according to Example 9) yielded 1-cyclohexyl-3-amino-4-methylmercapto-tetrahydro-1,3,5-triazine-2,6-dione as a colorless powder of melting point 177°-179° C.

EXAMPLE 11

Preparation of 1-benzyl-3-isopropylideneamine4-methyl-mercapto-tetrahydro-1,3,5-triazine2,6-dione.

(Compound 11)

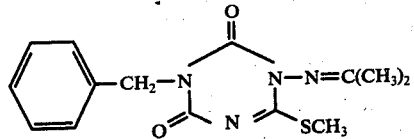

Analogously to Example 1, N-benzyl-bis-(chlorocarbonyl)-amine and acetone-S-methyl-isothiosemicarbazone hydroiodide, with addition of triethylamine, yielded 1-benzyl-3-isopropylideneamino-4-methylmercapto-tetrahydro-1,3,5-triazine-2,6-dione as a pale brown powder of melting point 148°-150° C.

EXAMPLE 12

Preparation of 1-benzyl-3-amino-4-methylmercaptotetrahydro-1,3,5-triazine-2,6-dione.

(Compound 12)

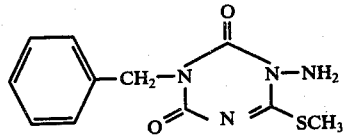

Analogously to Example 2, 1-benzyl-3-isopropylideneamino-4-methylmercapto-tetrahydro-1,3,5-triazine-2,6-dione (prepared according to Example 11) yielded 1-benzyl-3-amino4-methylmercapto-tetrahydro-1,3,5-triazine-2,6-dione as a colorless powder of melting point 127°-128° C.

EXAMPLE 13

Preparation of 1-phenyl-3-isopropylidene-amino-4-methylmercapto-tetrahydro-1,3,5-triazine-2,6-dione.

(Compound 13)

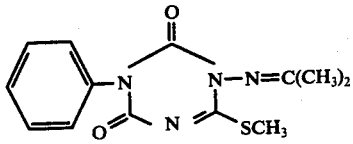

Analogously to Example 1, N-phenyl-bis-(chlorocarbonyl)-amine and acetone-S-methyl-isothiosemicarbazone hydro-iodide, with addition of triethylamine, yielded 1-phenyl-3-isopropylidene-amino-4-methylmercapto-tetrahydro-1,3,5-triazine-2,6-dione as a pale yellow powder of melting point 206°-207° C.

EXAMPLE 14

Preparation of 1-phenyl-3-amino-4-methylmercaptotetrahydro-1,3,5-triazine-2,6-dione.

(Compound 14)

Analogously to Example 2, 1-phenyl-3-isopropylidene-amino4-methylmercapto-tetrahydro-1,3,5-triazine-2,6-dione (prepared according to Example 13) yielded 1-phenyl-3-amino-4-methylmercapto-tetrahydro-1,3,5-triazine-2,6-dione as colorless needles of melting point 205°-208° C.

EXAMPLE 15

Preparation of 1-phenyl-3-amino-4-methylaminotetrahydro-1,3,5-triazine-2,6-dione.

(Compound 15)

Analogously to Example 3,1-phenyl3-amino-4-methylmercapto-tetrahydro-1,3,5-triazine-2,6-dione (prepared according to Example 14) and methylamine yielded 1-phenyl-3-amino-4-methylamino-tetrahydro-1,3,5-triazine-2,6-dione as a colorless powder of melting point 242°-244° C.

EXAMPLE 16

Preparationof 1-(4-methylphenyl)-3-isopropyl-ideneamino-4-methylmercapto-tetrahydro-1,3,5-triazine-2,6-dione.

Analogously to Example 1, N-(4-methylpehnyl)-bis(-chlorocarbonyl)-amine and acetone-S-methyl-isothiosemicarbazone hydroiodide, with addition of triethylamine, yielded 1-(4-methylphenyl)-3-isopropylideneamino-4-methylmercaptotetrahydro-1,3,5-triazine-2,6-dione as a yellow powder of melting point 170–173° C.

EXAMPLE 17

Preparation of 1-(4-methylphenyl)-3-amino-4-methylmercapto-tetrahydro-1,3,5-triazine-2,6-dione.

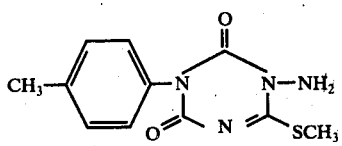

Analogously to Example 2, 1-(4-methylphenyl)-3-isopropylideneamino-4-methylmercapto-tetrahydro-1,3,5-triazine-2,6dione (prepared according to Example 16) yielded 1-(4-methylphenyl)-3-amino-4-methylmercapto-tetrahydro-1,3,5-triazine-2,6-dione as a colorless powder of melting point 196–197° C.

EXAMPLE 18

Preparation of 1-(4-methylphenyl)-3-amino-4-ethylamino-tetrahydro-1,3,5-triazine-2,6-dione.

(Compound 18)

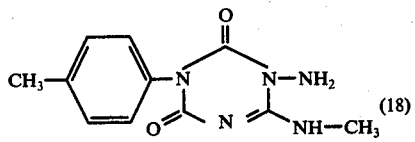

Analogously to Example 3, 1-(4-methylphenyl)-3-amino-4-methylmercapto-tetrahydro-1,3,5-triazine-2,6-dione (prepared according to Example 17) and methylamine, yielded 1-(4-methylphenyl)-3-amino-4-methylamino-tetrahydro-1,3,5-triazine-2,6-dione as a colorless powder of melting point 242–243° C.

EXAMPLE 19

Preparation of 1-(4-methylphenyl)-3-amino-4-ethylamino-tetrahydro-1,3,5-triazine-2,6-dione.

(Compound 19)

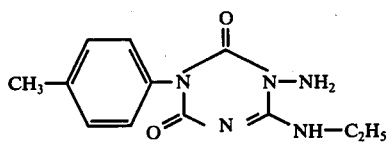

Analogously to Example 3, 1-(4-methylphenyl)-3-amino-4-methylmercapto-tetrahydro-1,3,5-triazine-2,6-dione (prepared according to Example 17) and ethylamine, yielded 1-(4-methylphenyl)-3-amino-4-ethylamino-tetrahydro-1,3,5-triazine-2,6-dione as colorless needles of melting point 247°–248° C.

EXAMPLE 20

Preparation of 1-(4-chlorophenyl)-3-isopropylideneamino-4-methylmercapto-tetrahydro-1,3,5-triazine-2,6-dione.

(Compound 20)

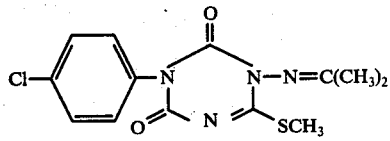

Analogously to Example 1, N-(4-chlorophenyl)-bis(-chlorocarbonyl)-amine and acetone-S-methyl-isothiosemicarbazone hydroiodide with addition of triethylamine, yielded 1-(4-chlorophenyl)-3-isopropylideneamino-4-methylmercaptotetrahydro-1,3,5-triazine-2,6-dione as a colorless powder of melting point 142°–144° C.

EXAMPLE 21

Preparation of 1-(4-chlorophenyl)-3-amino-4-methylmercapto-tetrahydro-1,3,5-triazine-2,6-dione.

(Compound 21)

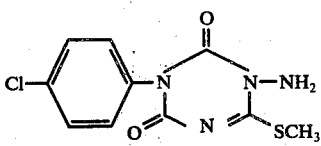

Analogously to Example 2, 1-(4-chlorophenyl)-3-isopropylideneamino-4-methylmercapto-tetrahydro-1,3,5-triazine-2,6-dione (prepared according to Example 20) yielded 1-(4-chlorophenyl)-3-amino-4-methylmercapto-tetrahydro-1,3,5-triazine-2,6-dione as a colorless powder of melting point 210°–212° C.

EXAMPLE 22

Preparation of 1-(3,4-dichlorophenyl)-3-isopropylideneamino-4-methylmercaptotetrahydro-1,3,5-triazine-2,6-dione.

(Compound 22)

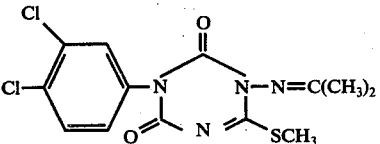

Analogously to Example 1, N-(3,4-dichlorophenyl)-bis(chlorocarbonyl)-amine and acetone-S-methyl-isothiosemicarbazone hydroiodide, with addition of triethylamine, yielded 1-(3,4-dichlorophenyl)-3-isopropylideneamino-4-methylmercapto-tetrahydro-1,3,5-triazine-2,6-dione as a colorless powder of melting point 181°–182° C.

EXAMPLE 23

Preparation of 1-(3,4-dichlorophenyl)-3-amino-4-methylmercapto-tetrahydro-1,3,5-triazine-2,6dione.

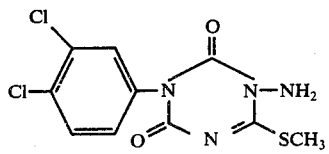

(Compound 23)

Analogously to Example 2, 1-(3,4-dichlorophenyl)-3-isopropylideneamino-4-methylmercapto-tetrahydro-1,3,5-triazine-2,6-dione (prepared according to Example 22) yielded 1-(3,4-dichlorophenyl)-3-amino-4-methylmercapto-tetrahydro-1,3,5-triazine-2,6-dione as a colorless powder of melting point 247° C (decomposition).

EXAMPLE 24

Preparation of 1,3-dimethyl-4-methylmercaptotetrahydro-1,3,5-triazine-2,6-dione.

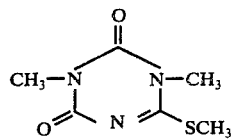

(Compound 24)

23.2 g (0.1 mole) of N,S-dimethyl-isothiourea hydroiodide were initially introduced into 100 ml of water and 250 ml of benzene. 15.6 (0.1 mole) of N-methyl-bis-(chlorocarbonyl)-amine in 100 ml of dry benzene and 12 g (0.3 mole) of sodium hydroxide dissolved in 100 ml of water were simultaneously slowly added dropwise from two dropping funnels with vigorous stirring. The reaction took place strongly exothermically. The mixture was stirred for a further hour, any product which precipitated was filtered off, and the benzene phase was separated off, dried over calcium chloride and evaporated in vacuo. The residue, together with the filter residue, was recrystallized from isopropanol. 14 g (75%) of 1,3-dimethyl-4-methylmercapto tetrahydro-1,3,5-triazine-2,6-dione were obtained as a colorless powder of melting point 137°–139° C.

EXAMPLE 25

Preparation of 1,3-dimethyl-4-methylaminotetrahydro-1,3,5-triazine-2,6-dione.

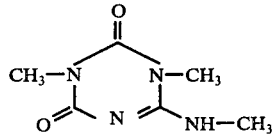

(Compound 25)

Analogously to Example 3, 1,3-dimethyl-4-methylmercaptotetrahydro-1,3,5-triazine-2,6-dione (prepared according to Example 24) and methylamine yielded 1,3-dimethyl-4-methylaminotetrahydro-1,3,5-triazine-2,6-dione as a colorless powder of melting point 294°–296° C.

EXAMPLE 26

Preparation of 1-methyl-3-ethyl-4-methylmercaptotetrahydro-1,3,5-triazine-2,6-dione.

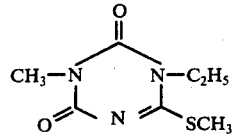

(Compound 26)

Analogously to Example 2, N-ethyl-S-methyl-isothiourea hydroiodide and N-methyl-bis-(chlorocarbonyl)-amine yielded 1-methyl-3-ethyl-4-methylmercapto-tetrahydro-1,3,5-triazine-2,6-dione as a colorless powder of melting point 118°–119° C.

EXAMPLE 27

Preparation of 1-methyl-3-butyl-4-methylmercaptotetrahydro-1,3,5-triazine-2,6-dione.

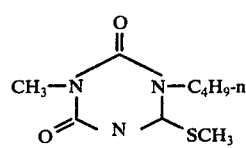

(Compound 27)

Analogously to Example 24, N-n-butyl-S-methyl-isothiourea hydroiodide and N-methyl-bis-(chlorocarbonyl)-amine yielded 1-methyl-3-butyl-4-methylmercapto-tetrahydro-1,3,5-triazine-2,6-dione, as a colorless powder of melting point 121°–122° C.

EXAMPLE 28

Preparation of 1-methyl-3-cyclohexyl-4-methylmercapto-tetrahydro-1,3,5-triazine-2,6-dione.

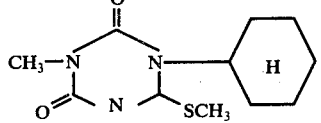

(Compound 28)

Analogously to Example 24, N-cyclohexyl-S-methylisothiourea hydroiodide and N-methyl-bis-(chlorocarbonyl)-amine yielded 1-amine-3-cyclohexyl-4-methylmercapto-tetrahydro-1,3,5-triazine-2,6-dione as a colorless powder of melting point 121°–122° C.

EXAMPLE 29

Preparation of 1-methyl-3-phenyl-4-methylmercaptotetrahydro-1,3,5-triazine-2,6-dione.

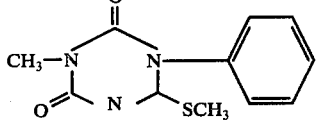

(Compound 29)

Analogously to Example 24, N-phenyl-S-methyl-isothiourea hydroiodide and N-methyl-bis-(chlorocarbonyl)-amine yielded 1-methyl-3-phenyl-4-methylmercapto-tetrahydro-1,3,5-triazine-2,6-dione as yellow needles of melting point 216°–217° C.

EXAMPLE 30

Preparation of
1-isopropyl-3-methyl-4-methylmercapto-tetrahydro-1,3,5-triazine-2,6-dione.

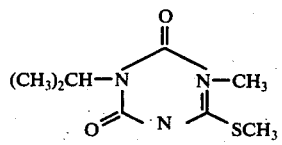

(Compound 30)

Analogously to Example 24, N,S-dimethyl-isothiourea hydroiodide and N-isopropyl-bis-(chlorocarbonyl)-amine (prepared analogously to Synthesis 1970, pages 542–543; boiling point 66–67° C/12 mm Hg yielded 1-isopropyl-3-methyl-4-methylmercapto-tetrahydro-1,3,5-triazine-2,6-dione as a colorless powder of melting point 73°–75° C.

EXAMPLE 31

Preparation of
1-isopropyl-3-methyl-4-methylaminotetrahydro-1,3,5-triazine-2,6-dione.

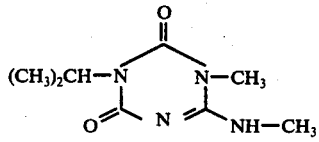

(Compound 31)

Analogously to Example 3, 1-isopropyl-3-methyl-4-methylmercapto-tetrahydro-1,3,5-triazine-2,6-dione (prepared according to Example 30) and methylamine yielded 1-isopropyl-3-methyl-4-methylamino-tetrahydro-1,3,5-triazine-2,6-dione as a colorless powder of melting point 224°–226° C.

EXAMPLE 32

Preparation of
1-isopropyl-3-ethyl-4-methylmercapto-tetrahydro-1,3,5-triazine-2,6-dione.

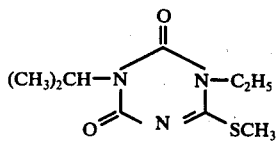

(Compound 32)

Analogously to Example 24, N-ethyl-S-methyl-isothiourea hydroiodide and N-isopropyl-bis-(chlorocarbonyl)-amine yielded 1-isopropyl-3-ethyl-4-methylmercapto-tetrahydro-1,3,5-triazine-2,6-dione as a colorless powder of melting point 198°–200° C.

EXAMPLE 33

Preparation of
1-isopropyl-3-phenyl-4-methylmercapto-tetrahydro-1,3,5-triazine-2,6-dione.

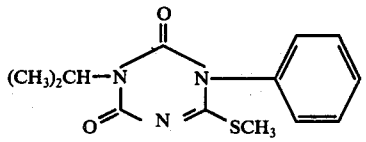

(Compound 33)

Analogously to Example 24, N-phenyl-S-methyl-isothiourea hydroiodide and N-isopropyl-bis-(chlorocarbonyl)-amine yielded 1-isopropyl-3-phenyl-4-methylmercapto-tetrahydro-1,3,5-triazine-2,6-dione as a colorless powder of melting point 137°–139° C.

EXAMPLE 34

Preparation of
1-cyclohexyl-3-methyl-4-methylmercapto-tetrahydro-1,3,5-triazine-2,6-dione.

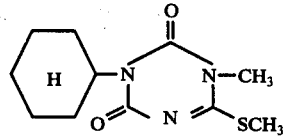

(Compound 34)

Analogously to Example 24, N,S-dimethyl-isothiourea hydroiodide and N-cyclohexyl-bis-(chlorocarbonyl)-amine (prepared analogously to Synthesis 1970, pages 542–543; boiling point 80°–82° C/0.3 mm Hg) yielded 1-cyclohexyl-3-methyl-4-methylmercapto-tetrahydro-1,3,5-triazine-2,6-dione as a colorless powder of melting point 135°–137° C.

EXAMPLE 35

Preparation of
1-phenyl-3-methyl-4-methylmercapto-tetrahydro-1,3,5-triazine-2,6-dione.

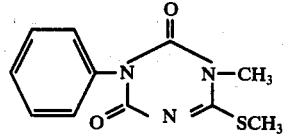

(Compound 35)

Analogously to Example 24, N,S-dimethyl-isothiourea hydroiodide and N-phenyl-bis-(chlorocarbonyl)-amine yielded 1-phenyl-3-methyl-4-methylmercapto-tetrahydro-1,3,5-triazine-2,6-dione as colorless flakes of melting point 236°–239° C.

EXAMPLE 36

Preparation of
1-phenyl-3-methyl-4-methylamino-tetrahydro-1,3,5-triazine-2,6-dione.

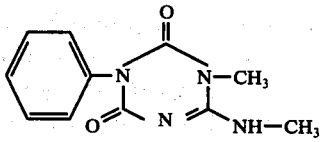

(Compound 36)

Analogously to Example 3, 1-phenyl-3-methyl-4-methylmercapto-tetrahydro-1,3,5-triazine-2,6-dione (prepared according to Example 35) and methylamine yielded 1-phenyl-3-methyl-4-methylamino-tetrahydro-1,3,5-triazine-2,6-dione as a colorless powder of melting point 297°–299° C.

EXAMPLE 37

Preparation of 1-phenyl-3-ethyl-4-methylmercapto-tetrahydro-1,3,5-triazine-2,6-dione.

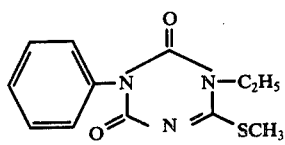

(Compound 37)

Analogously to Example 24, N-ethyl-S-methyl-isothiourea hydroiodide and N-phenyl-bis-(chlorocarbonyl)-amine yielded 1-phenyl-3-ethyl-4-methylmercapto-tetrahydro-1,3,5-triazine-2,6-dione as a colorless powder of melting point 149°–150° C.

EXAMPLE 38

Preparation of 1-phenyl-3-n-propyl-4-methylmercapto-tetrahydro-1,3,5-triazine-2,6-dione.

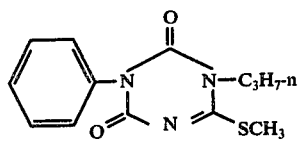

(Compound 38)

Analogously to Example 24, N-n-propyl-S-methyl-isothiourea hydroiodide and N-phenyl-bis-(chlorocarbonyl)-amine yielded 1-phenyl-3-n-propyl-4-methylmercapto-tetrahydro-1,3,5-triazine-2,6-dione as a colorless powder of melting point 124°–126° C.

EXAMPLE 39

Preparation of 1,3-diphenyl-4-methylmercapto-tetrahydro-1,3,5-triazine-2,6-dione.

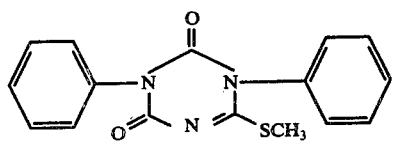

(Compound 39)

Analogously to Example 24, N-phenyl-S-methyl-isothiourea hydroiodide and N-phenyl-bis-(chlorocarbonyl)-amine yielded 1,3-diphenyl-4-methylmercapto-tetrahydro-1,3,5-triazine-2,6-dione as colorless needles of melting point 219°–220° C.

EXAMPLE 40

Preparation of 1-(4-chlorophenyl)-3-methyl-4-methylmercapto-tetrahydro-1,3,5-triazine-2,6-dione.

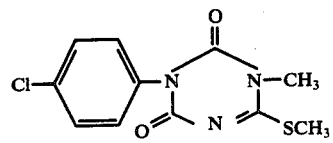

(Compound 40)

Analogously to Example 24, N,S-dimethyl-isothiourea hydroiodide and N-(4-chlorophenyl)-bis-(chlorocarbonyl)-amine yielded 1-(4-chlorophenyl)-3-methyl-4-methylmercapto-tetrahydro-1,3,5-triazine-2,6-dione as a colorless powder of melting point 146°–148° C.

EXAMPLE 41

Preparation of 1-(4-chlorophenyl)-3-methyl-4-methylamino-tetrahydro-1,3,5-triazine-2,6-dione.

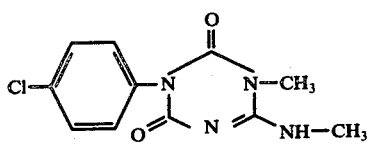

(Compound 41)

Analogously to Example 3, 1-(4-chlorophenyl)-3-methyl-4-methylmercapto-tetrahydro-1,3,5-triazine-2,6-dione (prepared according to Example 40) and methylamine yielded 1-(4-chlorophenyl)-3-methyl-4-methylamino-tetrahydro-1,3,5-triazine-2,6-dione as a colorless powder of melting point 312°–313° C.

EXAMPLE 42

Preparation of 1-(4-chlorophenyl)-3-ethyl-4-methylmercapto-tetrahydro-1,3,5-triazine-2,6-dione.

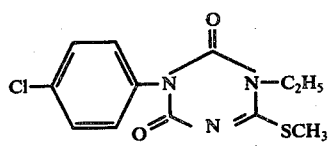

(Compound 42)

Analogously to Example 24, N-ethyl-S-methyl-isothiourea hydroiodide and N-(4-chlorophenyl)-bis-(chlorocarbonyl)-amine yielded 1-(4-chlorophenyl)-3-ethyl-4-methylmercapto-tetrahydro-1,3,5-triazine-2,6-dione as a colorless powder of melting point 198°–200° C.

EXAMPLE 43

Preparation of 1-methyl-4-ethyl-tetrahydro-1,3,5-triazine-2,6-dione.

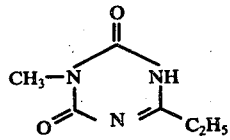

(Compound 43)

10.9 g (0.1 mole) of propionamidine hydrochloride were suspended in 125 ml of water and 200 ml of benzene. 15.6 g (0.1 mole) of N-methyl-bis-(chlorocarbonyl)-amine in 100 ml of dry benzene and 18 g (0.45 mole) of sodium hydroxide dissolved in 100 ml of water were simultaneously slowly added dropwise from two dropping funnels, with vigorous stirring. The reaction took place exothermically. The mixture was stirred for a further hour, the aqueous phase was separated off and acidified with glacial acetic acid and the mixture was evaporated in vacuo. The residue was repeatedly extracted by boiling with ethyl acetate. The solution was concentrated in vacuo and cooled. The precipitate was filtered off. 7.8 g (50%) of 1-methyl-4-ethyl-tetrahydro-1,3,5-triazine-2,6-dione were obtained as colorless needles of melting point 202°-203° C.

EXAMPLE 44

Preparation of 1-isopropyl-4-ethyl-tetrahydro-1,3,5-triazine-2,6-dione.

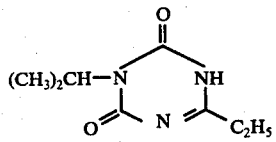

(Compound 44)

Analogously to Example 43, propionamidine hydrochloride and N-isopropyl-bis-(chlorocarbonyl)-amine yielded 1-isopropyl-4-ethyl-tetrahydro-1,3,5-triazine-2,6-dione as colorless needles of melting point 146°-148° C.

EXAMPLE 45

Preparation of 1-phenyl-4-methyl-tetrahydro-1,3,5-triazine-2,6-dione.

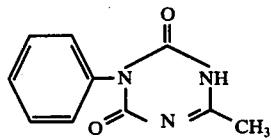

(Compound 45)

Analogously to Example 43, acetamidine hydrochloride and N-phenyl-bis-(chlorocarbonyl)-amine yielded 1-phenyl-4-methyltetrahydro-1,3,5-triazine-2,6-dione as a colorless powder of melting point 245°-247° C.

EXAMPLE 46

Preparation of 1-phenyl-4-ethyl-tetrahydro-1,3,5-triazine-2,6-dione.

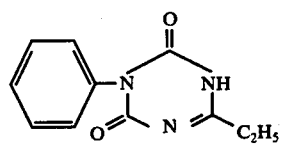

(Compound 46)

Analogously to Example 43, propionamidine hydrochloride and N-phenyl-bis-(chlorocarbonyl)-amine yielded 1-phenyl-4-ethyl-tetrahydro-1,3,5-triazine-2,6-dione as colorless needles of melting point 172°-175° C.

EXAMPLE 47

Preparation of 1-phenyl-3-acetoxy-4-ethyl-tetrahydro-1,3,5-triazine-2,6-dione.

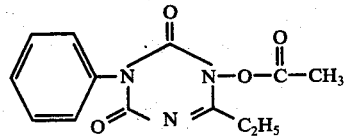

(Compound 47)

13 g (0.1 mole) of 0-acetyl-propionamidoxime (melting point: 80°-83° C) were initially introduced into 100 ml of benzene. 21.8 g (0.1 mole) of N-phenyl-bis-(chloro-carbonyl)-amine in 100 ml of benzene were added dropwise and this was followed by the slow dropwise addition of 20.2 g (0.2 mole) of triethylamine in 50 ml of benzene. The reaction was exothermic. The mixture was stirred for a further hour, the precipitate was filtered off and the benzene filtrate was concentrated in vacuo. The residue was recrystallized from isopropanol. 14 g (51%) of 1-phenyl-3-acetoxy-4-ethyl-tetrahydro-1,3,5-triazine-2,6-dione were obtained as colorless needles of melting point 128°-130° C.

The compounds listed in Table 1 below were prepared analogously to Example 1:

Table 1

| Example No. | $R^1$ | $R^3$ | Melting point, ° C |
|---|---|---|---|
| 48 | $CH_3$ | $-S-C_2H_5$ | 118 - 120 |
| 49 | $C_4H_9$ | $-S-C_2H_5$ | 81 - 83 |
| 50 | cyclohexyl-H | $-S-C_2H_5$ | 94 - 96 |
| 51 | $C_2H_5-$ | $-S-CH_3$ | 151 - 152 |
| 52 | $C_3H_7$ | $-S-CH_3$ | 92 - 93 |
| 53 | $C_4H_9$ | $-S-CH_3$ | red oil |
| 54 | $(CH_3)_2CH-CH_2-$ | $-S-CH_3$ | 127 - 128 |
| 55 | $C_2H_5-CH(CH_3)-$ | $-S-CH_3$ | 74 - 76 |
| 56 | $C_{12}H_{25}-$ | $-S-CH_3$ | 95 - 96 |
| 57 | 2,4-Cl-phenyl | $-S-CH_3$ | 183 - 184 |
| 58 | 4-$CF_3$-phenyl | $-S-CH_3$ | 135 - 136 |
| 59 | 3-$CF_3$-phenyl | $-S-CH_3$ | 155 - 156 |
| 60 | 3-$CH_3O$-4-Cl-phenyl | $-S-CH_3$ | 177 - 178 |

The compounds listed in Table 2 below were prepared analogously to Example 1.

Table 2

$$\text{structure: 1,3,5-triazine ring with } R^1-N, N-R^2, =O \text{ at positions, and } S-CH_3$$

| Example No. | $R^1$ | $R^2$ | Melting point, °C |
|---|---|---|---|
| 61 | $(CH_3)_2CH$ | $-N=CH-CH(CH_3)_2$ | 94 – 97 |
| 62 | $(CH_3)_2CH$ | $-N=CH-C_6H_5$ | 108 – 110 |
| 63 | $(CH_3)_2CH$ | $-N=CH-$(2-furyl) | 151 – 153 |
| 64 | $(CH_3)_2CH$ | $-N=CH-C_6H_4-NO_2$ | 198 – 200 |
| 65 | $(CH_3)_2CH-CH_2$ | $-N=CH-CH(CH_3)_2$ | 67 – 69 |
| 66 | $(CH_3)_2CH-CH_2$ | $-N=CH-C_6H_5$ | 140 – 143 |
| 67 | $C_2H_5-CH(CH_3)-$ | $-N=CH-C_6H_5$ | 101 – 103 |
| 68 | $C_2H_5-CH(CH_3)-$ | $-N=CH-C_6H_4-NO_2$ | 138 – 140 |
| 69 | $C_2H_5-CH(CH_3)-$ | $-N=CH-$(2-furyl) | 134 – 136 |
| 70 | cyclohexyl | $-N=CH-CH(CH_3)_2$ | 103 – 106 |
| 71 | cyclohexyl | $-NH-CH(OH)-CCl_3$ | 159 – 160 |
| 72 | cyclohexyl | $-N=CH-C_6H_5$ | 138 – 141 |
| 73 | cyclohexyl | $-N=CH-C_6H_4-NO_2$ | 208 – 209 |
| 74 | cyclohexyl | $-N=CH-$(2-furyl) | 133 – 135 |

The compounds listed in Table 3 below were prepared analogously to Example 2.

Table 3

$$\text{structure: 1,3,5-triazine with } R^1-N, N-NH_2, =O, S-CH_3$$

| Example No. | $R^1$ | Melting point, °C |
|---|---|---|
| 75 | $C_2H_5$ | 199 – 201 |
| 76 | $C_3H_7$ | 131 – 132 |
| 77 | $C_4H_9$ | 133 – 134 |
| 78 | $(CH_3)_2CH-CH_2-$ | 166 – 168 |

Table 3-continued

Structure:
$$R^1-N(-C(=O)-)N(-NH_2)-C(-S-CH_3)=N-$$ (6-membered ring with two C=O)

| Example No. | R¹ | Melting point, °C |
|---|---|---|
| 79 | C₂H₅—CH(CH₃)— | 151 – 152 |
| 80 | C₁₂H₂₅ | 116 – 118 |
| 81 | 2,4-dichlorophenyl | 237 – 238 |
| 82 | 3-(trifluoromethyl)phenyl | 195 – 198 |
| 83 | 3-chloro-4-methylphenyl | 220 – 223 |

The compounds listed in Table 4 below were prepared analogously to Example 3.

Table 4

Structure:
$$R^1-N(-C(=O)-)N(-NH_2)-C(R^3)=N-$$ (6-membered ring with two C=O)

| Ex. No. | R¹ | R³ | Melting point, °C |
|---|---|---|---|
| 84 | C₂H₅ | NH—CH₃ | 162-164 |
| 85 | C₂H₅ | NH—C₂H₅ | 194-195 |
| 86 | C₂H₅ | NH—CH(CH₃)₂ | 147-150 |
| 87 | C₃H₇ | NH—CH₃ | 144-145 |
| 88 | C₃H₇ | NH—C₂H₅ | 130-133 |
| 89 | C₃H₇ | NH—CH(CH₃)₂ | 123-124 |
| 90 | C₃H₇ | N(CH₃)₂ | 104-105 |
| 91 | (CH₃)₂CH | NH—CH(CH₃)₂ | 158-160 |
| 92 | (CH₃)₂CH | NH—CH₂—CH(CH₃)₂ | 154-156 |
| 93 | (CH₃)₂CH—CH₂ | NH—CH₃ | 160-161 |
| 94 | (CH₃)₂CH—CH₂ | NH—C₂H₅ | 142-144 |
| 95 | (CH₃)₂CH—CH₂ | NH—CH(CH₃)₂ | 136-138 |
| 96 | C₂H₅—CH(CH₃)— | NH—CH₃ | 150-151 |
| 97 | C₂H₅—CH(CH₃)— | NH—C₂H₅ | 104-106 |
| 98 | C₂H₅—CH(CH₃)— | NH—CH(CH₃)₂ | 145-146 |
| 99 | C₂H₅—CH(CH₃)— | NH—C₄H₉ | 120-121 |
| 100 | C₁₂H₂₅ | NH—CH₃ | 148-149 |
| 101 | cyclohexyl | NH—CH₃ | 169-171 |
| 102 | cyclohexyl | NH—C₂H₅ | 178-179 |
| 103 | cyclohexyl | NH—CH(CH₃)₂ | 169-172 |
| 104 | cyclohexyl | N(CH₃)₂ | 207-210 |
| 105 | phenyl | NH—C₂H₅ | 234-235 |
| 106 | phenyl | N(CH₃)₂ | 172-173 |
| 107 | (CH₃)₂CH | NH₂ | 246-248 |
| 108 | C₂H₅—CH(CH₃)— | NH₂ | 188-190 |
| 109 | cyclohexyl | NH₂ | 263-265 |
| 110 | C₃H₇ | NH—NH₂ | 234 (decomp.) |
| 111 | (CH₃)₂CH | NH—NH₂ | 224 (decomp.) |
| 112 | (CH₃)₂CH—CH₂ | NH—NH₂ | 229-230 |
| 113 | C₂H₅—CH(CH₃)— | NH—NH₂ | 179-181 |
| 114 | cyclohexyl | NH—NH₂ | 273 (decomp.) |
| 115 | (CH₃)₂CH—CH₂ | NH—OH | 260 (decomp.) |
| 116 | cyclohexyl | NH—OH | 225 (decomp.) |
| 117 | phenyl | NH—OH | 208 (decomp.) |

Using the 3-isopropylideneamino compounds (obtained according to Example 1) and heating the mixture under anhydrous conditions, the compounds listed in Table 5 below were obtained analogously to Example 3:

Table 5

Structure:
$$R^1-N(-C(=O)-)N(-N=C(CH_3)_2)-C(R^3)=N-$$ (6-membered ring with two C=O)

| Ex. No. | R¹ | R³ | Melting point, °C |
|---|---|---|---|
| 118 | (CH₃)₂CH—CH₂ | N(CH₃)₂ | 60-61 |
| 119 | cyclohexyl | N(CH₃)₂ | 156-158 |
| 120 | phenyl | N(CH₃)₂ | 168-172 |

The active compounds according to the invention display strong herbicidal properties and can therefore be used for combating weeds. By weeds, in the broadest sense, there are to be understood all plants which grow in locations where they are not desired. Since the active compounds influence plant growth in different ways, they can be employed as selective herbicides. At higher concentrations (for instance 25 kg/ha), the active compounds according to the invention are suitable for the total combating of weeds.

The active compounds according to the invention can be employed in the case of, for example, the following plants: dicotyledons, such as mustard (*Sinapis*), cress (*Lepidiumv*), cleavers (*Galium*), chickweed (*Stellaria*), camomile (*Matricaria*), gallant soldier (*Galinsoga*), goosefoot (*Chenopodium*), annual nettle (*Urtica*), groundsel (*Senecio*), cotton (*Gossypium*), beets (*Beta*), carrots (*Daucus*), beans (*Phaseolus*), potatoes (*Solanum*) and coffee (*Coffea*); monocotyledons, such as timothy (*Phleum*), bluegrass (*Poa*), fescue (*Festuca*), goosegrass (*Eleusine*), foxtail (*Setaria*), ryegrass (*Lolium*), cheat (*Bromus*), barnyard grass (*Echinochloa*), maize (*Zea*), rice (*Oryza*), oats (*Avena*), barley (*Hordeum*), wheat (*Triticum*), millet (*Panicum*) and sugar cane (*Saccharum*).

The active compounds are particularly suitable for the selective combating of weeds in cotton, maize, cereals and carrots.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents includes non-ionic and anionic emulsifiers, such as polyoxyethylene-fatty acids esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds.

The formulations generally contain from 0.1 to 95 percent by weight, preferably from 0.5 to 90 percent by weight of active compound.

The active compounds can be used as such, in the form of their formulations or in the application forms prepared therefrom, such as ready-to-use solutions, emulsions, suspensions, powders, pastes and granules. They can be used in the customary manner, for example by watering, spraying atomising, sprinkling and dusting.

They can be used either by the post-emergence process or by the pre-emergence process. The amount of active compound employed can fluctuate within fairly wide ranges. It depends essentially on the nature of the desired effect. In general, the amounts used are between 0.1 and 20 kg of active compound/ha, preferably between 0.5 and 15 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention thus enables providing crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the compounds of this invention is illustrated in the following test Examples. The compounds of this invention are each identified by the number of the corresponding preparative Example hereinafter; the known compounds, used for comparison, are as follows:

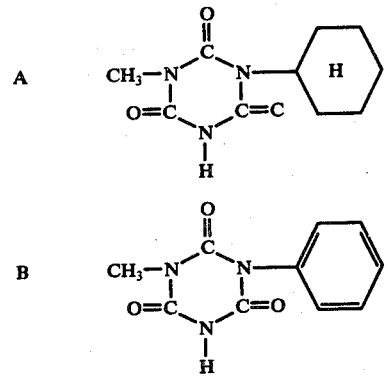

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants, which had a height of 5-15 cm, were sprayed with the preparation of the active compound in such a way that the amounts of active compound per unit area shown in the table were applied. Depending on the concentration of the spray liquor, the amount of water used was between 1,000 and 2,000 l/ha. After three weeks, the degree of damage to the plants was determined and characterised by the values 0-5, which had the following meaning:

0 no effect
1 a few slightly burnt spots
2 marked damage to leaves
3 some leaves and parts of stalks partially dead
4 plant partially destroyed
5 plant completely dead.

The active compounds, amounts used and results can be seen from the table which follows:

To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterised by the values 0-5, which had the following meaning:

0 no effect
1 slight damage or delay in growth
2 marked damage or inhibition of growth
3 heavy damage and only deficient development or Table A

| Active compound No. | Amount of active compound used, kg/ha | Echino-chloa | Cheno-podium | Sina-psi | Galin-soga | Stell-aria | Matri-caria | Carrots | Oats | Cotton | Wheat | Beans |
|---|---|---|---|---|---|---|---|---|---|---|---|---|
| 4 | 1 | 4-5 | 5 | 5 | 5 | 5 | 5 | 5 | 4-5 | 5 | 5 | 5 |
|   | 0.5 | 4 | 5 | 5 | 5 | 4 | 4 | 5 | 4 | 5 | 5 | 4 |
| 44 | 1 | 4 | 5 | 5 | 4-5 | 5 | 4 | 1 | 3 | 3 | 4 | 4 |
|   | 0.5 | 3 | 4 | 5 | 4 | 4-5 | 4 | 0 | 2-3 | 2 | 3 | 3 |
| 5 | 1 | 5 | 5 | 5 | 5 | 5 | 5 | 5 | 5 | 5 | 5 | 5 |
|   | 0.5 | 5 | 5 | 5 | 5 | 5 | 5 | 5 | 5 | 5 | 5 | 5 |
| 6 | 1 | 5 | 5 | 5 | 5 | 5 | 5 | 5 | 5 | 5 | 4-5 | 5 |
|   | 0.5 | 5 | 5 | 5 | 5 | 5 | 5 | 5 | 3 | 5 | 3 | 5 |
| 31 | 1 | 5 | 5 | 5 | 5 | 5 | 4-5 | 5 | 4-5 | 3 | 2 | 5 |
|   | 0.5 | 4 | 5 | 5 | 5 | 4 | 4 | 4 | 4 | 3 | 1 | 4-5 |
| 34 | 1 | 5 | 4-5 | 5 | 5 | 4 | 5 | 3 | 4 | 2 | 1 | 4-5 |
|   | 0.5 | 4-5 | 4 | 5 | 5 | 3 | 4-5 | 2 | 3 | 1 | 0 | 3 |
| 10 | 1 | 5 | 5 | 5 | 5 | 5 | 5 | 5 | 5 | 5 | 5 | 5 |
|   | 0.5 | 5 | 5 | 5 | 5 | 5 | 5 | 5 | 5 | 5 | 5 | 5 |
| 77 | 1 | 5 | 5 | 5 | 5 | 5 | 5 | 5 | 4 | 5 | 2 | 5 |
|   | 0.5 | 3 | 5 | 3 | 5 | 5 | 5 | 4 | 3 | 4 | 2 | 5 |
| 76 | 1 | 5 | 5 | 5 | 5 | 5 | 5 | 3 | 4 | 3 | 2 | 4-5 |
|   | 0.5 | 3 | 4 | 3 | 5 | 4 | 3 | 2 | 3 | 2 | 1 | 4 |
| 101 | 1 | 5 | 5 | 5 | 5 | 5 | 5 | 5 | 5 | 5 | 4 | 5 |
|   | 0.5 | 5 | 5 | 5 | 5 | 5 | 5 | 5 | 5 | 5 | 3 | 5 |
| 103 | 1 | 5 | 5 | 5 | 5 | 5 | 5 | 5 | 3 | 5 | 4 | 5 |
|   | 0.5 | 4 | 5 | 5 | 5 | 5 | 5 | 5 | 2 | 5 | 2 | 5 |
| 87 | 1 | 5 | 5 | 5 | 5 | 3 | 5 | 5 | 4 | 5 | 4 | 5 |
|   | 0.5 | 3 | 5 | 5 | 5 | 3 | 3 | 4 | 3 | 5 | 3 | 5 |
| 93 | 1 | 4 | 5 | 5 | 5 | 5 | 4 | 5 | 4 | 5 | 3 | 5 |
|   | 0.5 | 3 | 5 | 5 | 5 | 4 | 3 | 5 | 3 | 5 | 2 | 5 |
| 90 | 1 | 5 | 5 | 5 | 5 | 5 | 5 | 5 | 5 | 5 | 3 | 5 |
|   | 0.5 | 4 | 5 | 5 | 5 | 5 | 5 | 5 | 4 | 5 | 2 | 5 |
| 104 | 1 | 5 | 5 | 5 | 5 | 5 | 5 | 5 | 4-5 | 5 | 4 | 5 |
|   | 0.5 | 5 | 5 | 5 | 5 | 5 | 5 | 5 | 4 | 5 | 4 | 5 |
| 105 | 1 | 5 | 5 | 5 | 5 | 5 | 5 | 5 | 4-5 | 5 | 4 | 5 |
|   | 0.5 | 5 | 5 | 5 | 5 | 5 | 4-5 | 5 | 3 | 5 | 3 | 5 |
| A (known) | 1 | 1 | 0 | 0 | 0 | 0 | 0 | 0 | 0 | 0 | 0 | 1 |
|   | 0.5 | 1 | 0 | 0 | 0 | 0 | 0 | 0 | 0 | 0 | 0 | 0 |
| B (known) | 1 | 2 | 2 | 4 | 0 | 0 | 1 | 0 | 2 | 0 | 0 | 2 |
|   | 0.5 | 1 | 1 | 4 | 0 | 0 | 0 | 0 | 2 | 0 | 0 | 2 |

EXAMPLE B

Pre-emergence test
Solvent: 5 parts by weight of acetone
Emulsifier: 1 part by weight of alkylaryl polyglycol ether only 50% emerged
4 plants partially destroyed after germination or only 25% emerged
5 plants completely dead or not emerged.

The active compounds, the amounts applied and the results obtained can be seen from the following table:

Table B

| Active compound No. | Amount of active compound used, kg/ha | Echino-chloa | Cheno-podium | Sina-psi | Lol-ium | Stell-aria | Galin-soga | Matri-caria | Avena fatua | Cotton | Wheat | Buck wheat | Maize |
|---|---|---|---|---|---|---|---|---|---|---|---|---|---|
| 13 | 5 | 5 | 5 | 5 | 5 | 5 | 5 | 5 | 5 | 3 | 5 | 3 |
|   | 2.5 | 4 | 5 | 4 | 5 | 5 | 5 | 5 | 5 | 5 | 3 | 5 | 2 |
| 14 | 5 | 5 | 5 | 5 | 5 | 5 | 5 | 5 | 4 | 2 | 3 | 4-5 | 2 |
|   | 2.5 | 4 | 5 | 4 | 5 | 5 | 5 | 3 | 1 | 3 | 3 | 1 |
| 4 | 5 | 5 | 5 | 5 | 5 | 5 | 5 | 5 | 4-5 | 3 | 5 | 3 |
|   | 2.5 | 5 | 5 | 5 | 5 | 5 | 5 | 5 | 5 | 4 | 3 | 4-5 | 2 |

Table B-continued

Pre-emergence test

| Active compound No. | Amount of active compound used, kg/ha | Echino-chloa | Cheno-podium | Sina-pis | Lol-ium | Stell-aria | Galin-soga | Matri-caria | Avena fatua | Cotton | Wheat | Buck wheat | Maize |
|---|---|---|---|---|---|---|---|---|---|---|---|---|---|
| 5 | 5 | 5 | 5 | 5 | 5 | 5 | 5 | 5 | 4–5 | 5 | 5 | 4–5 | 2 |
|   | 2.5 | 5 | 4–5 | 5 | 5 | 5 | 5 | 5 | 4 | 4 | 4 | 4 | 1 |
| 9 | 5 | 5 | 5 | 4–5 | 5 | — | 5 | 5 | 4–5 | 3 | 3 | 5 | 4 |
|   | 2.5 | 5 | 4 | 4–5 | 4–5 | — | 5 | 5 | 4 | 2 | 2 | 3 | 3 |
| 6 | 5 | 5 | 5 | 5 | 5 | — | 5 | 5 | 4–5 | 3 | 1 | 4–5 | 2–3 |
|   | 2.5 | 5 | 5 | 5 | 5 | — | 5 | 5 | 4 | 3 | 0 | 4–5 | 1 |
| 31 | 5 | 5 | 5 | 5 | 4–5 | — | 5 | 5 | 5 | 4 | 3 | 4–5 | 3 |
|   | 2.5 | 4 | 4–5 | 4–5 | 4 | — | 5 | 4–5 | 4 | 3 | 2 | 4–5 | 3 |
| 10 | 5 | 5 | 5 | 5 | 5 | — | 5 | 5 | 5 | 3 | 2 | 5 | 4 |
|   | 2.5 | 5 | 4 | 4–5 | 5 | — | 5 | 5 | 5 | 2 | 1 | 4 | 4 |
| 77 | 5 | 5 | 5 | 2 | 4–5 | — | 5 | 5 | 4 | 3 | 3 | 3 | 3 |
|   | 2.5 | 5 | 4 | 2 | 4 | — | 5 | 5 | 3 | 2 | 2 | 3 | 2 |
| 76 | 5 | 5 | 5 | 5 | 5 | — | 5 | 5 | 5 | 4 | 3 | 5 | 3 |
|   | 2.5 | 5 | 5 | 5 | 5 | — | 5 | 5 | 4 | 4 | 3 | 5 | 3 |
| 101 | 5 | 5 | 5 | 5 | 5 | — | 5 | 5 | 5 | 4 | 3 | 5 | 4 |
|   | 2.5 | 5 | 5 | 5 | 5 | — | 5 | 5 | 5 | 4 | 2 | 5 | 3 |
| 103 | 5 | 5 | 5 | 4 | 5 | — | 5 | 5 | 3 | 2 | 2 | 4 | 3 |
|   | 2.5 | 5 | 5 | 4 | 4 | — | 5 | 5 | 2 | 2 | 1 | 2 | 3 |
| 87 | 5 | 5 | 5 | 4 | 3 | — | 5 | 5 | 3 | 4 | 3 | 4 | 3 |
|   | 2.5 | 4 | 4 | 4 | 2 | — | 5 | 5 | 3 | 3 | 2 | 3 | 2 |
| 93 | 5 | 5 | 5 | 5 | 4 | — | 5 | 5 | 3 | 3 | 3 | 4–5 | 3 |
|   | 2.5 | 5 | 5 | 5 | 4 | — | 5 | 5 | 2 | 2 | 3 | 3 | 3 |
| 90 | 5 | 5 | 5 | 5 | 5 | — | 5 | 5 | 5 | 4 | 4 | 5 | 3 |
|   | 2.5 | 5 | 5 | 5 | 5 | — | 5 | 5 | 4 | 3 | 4 | 5 | 3 |
| 104 | 5 | 5 | 5 | 5 | 5 | — | 5 | 5 | 4 | 3 | 3 | 5 | 4 |
|   | 2.5 | 5 | 5 | 5 | 5 | — | 5 | 5 | 4 | 2 | 3 | 5 | 3 |
| 105 | 5 | 5 | 5 | 5 | 5 | — | 5 | 5 | 5 | 2 | 3 | 4–5 | 4 |
|   | 2.5 | 5 | 5 | 5 | 5 | — | 5 | 5 | 5 | 2 | 3 | 3 | 3 |
| A (known) | 5 | 0 | 0 | 0 | 0 | — | 0 | 0 | 0 | 0 | 0 | 0 | 0 |
|   | 2.5 | 0 | 0 | 0 | 0 | — | 0 | 0 | 0 | 0 | 0 | 0 | 0 |
| B (known) | 5 | 1 | 0 | 2 | 0 | — | 4 | 4 | 1 | 0 | 0 | 2 | 1 |
|   | 2.5 | 0 | 0 | 0 | 0 | — | 3 | 2 | 0 | 0 | 0 | 1 | 0 |

It will be understood that the foregoing specification and examples are illustrative but not limitative of the present invention inasmuch as other embodiments within the spirit and scope of the invention will suggest themselves to those skilled in the art.

What is claimed is:

1. 1 (3-times amended) Tetrahydro-1,3,5-triazine-2,6-dione compound of the formula

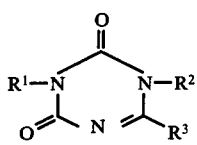

wherein

R¹ is alkyl of from 1 to 12 carbon atoms, haloalkyl of from 1 to 12 carbon atoms, cycloalkyl of from 5 to 7 ring carbon atoms, carbocyclic aralkyl of up to 12 carbon atoms or carbocyclic aryl of up to 10 carbon atoms, which cycloalkyl, carbocyclic aralkyl or carbocyclic aryl may be substituted with at least one of halogen, alkyl of up to 4 carbon atoms, alkoxy of up to 4 carbon atoms and trifluoromethyl, R² is alkoxy or alkanoyloxy of from 1 to 4 carbon atoms, cycloalkyl of from 5 to 7 ring carbon atoms, carbocyclic aralkyl of up to 12 carbon atoms or carbocyclic aryl of up to 10 carbon atoms; or R² is —NR⁴R⁵ wherein R⁴ and R⁵ individually represent hydrogen, alkyl of up to 4 carbon atoms or alkanoyl of up to 4 carbon atoms; or R² is —NR⁴R⁵ wherein R⁴ and R⁵ together represent alkylidene, of up to 3 carbon atoms, optionally substituted with at least one of carbocyclic aryl, haloaryl, alkoxyaryl and nitroaryl of up to 10 carbon atoms;

R³ is hydrogen, halogen, alkyl of up to 10 carbon atoms, haloalkyl of up to 10 carbon atoms or carbocyclic aryloxy of up to 10 carbon atoms; or R³ is —N—R⁶R⁷ wherein R⁶ and R⁷ individually are hydrogen, alkyl of up to 4 carbon atoms, carbocyclic aralkyl of up to 7 carbon atoms, hydroxyl, amino, or methoxy; or R³ is alkoxy or alkylthio of up to 4 carbon atoms.

2. Dione compound as claimed in claim 1 wherein R¹ is alkyl of from 1 to 12 carbon atoms, haloalkyl of from 1 to 12 carbon atoms, cycloalkyl of from 5 to 7 ring carbon atoms, benzyl or phenyl which may be substituted by at least one of chlorine, methylmethoxy and trifluoromethyl.

3. Dione compound as claimed in claim 1 wherein R² is cycloalkyl of from 5 to 7 ring carbon atoms, phenyl or acetyloxy.

4. Dione compound as claimed in claim 1 wherein R² is —NR⁴R⁵ wherein R⁴ and R⁵ individually represent hydrogen, alkyl of up to 4 carbon atoms or alkanoyl of up to 4 carbon atoms.

5. Dione compound as claimed in claim 4 wherein R³ is alkoxy or alkylmercapto.

6. Dione compound as claimed in claim 5 wherein R¹ is branched alkyl of up to 12 carbon atoms.

7. Dione compound as claimed in claim 6 wherein R³ is sec-butyl.

8. Dione compound as claimed in claim 7 designated 1-sec.-butyl-3-amino-4-methylthio-tetrahydro-1,3,5-triazine-2,6-dione.

9. Dione compound as claimed in claim 1 wherein R² is —NR⁴R⁵ wherein R⁴ and R⁵ together represent alkylidene, otpionally substituted with at least one of aryl, haloaryl, alkoxyaryl and nitroaryl of up to 10 carbon atoms.

10. Dione compound as claimed in claim 1 wherein R³ is hydrogen, halogen, alkyl, haloalkyl or aryloxy of up to 10 carbon atoms.

11. Dione comound as claimed in claim 1 wherein $R^3$ is alkyl of from 1 to 4 carbon atoms.

12. Dione compound as claimed in claim 1 wherein $R^3$ is alkoxy or alkylmercapto of up to 6 carbon atoms.

13. Dione compound as claimed in claim 1 wherein $R^2$ is —$NR^4R^5$ and $R^4$ and $R^5$ together represent cycloalkylidene.

14. Dione compound as claimed in claim 1 designated 1-isopropyl-3-isopropylideneamino-4-methylmercapto-tetrahydro-1,3,5-triazine-2,6-dione.

15. Dione compound as claimed in claim 1 designated 1-isopropyl-3-amino-4-methylamino-tetrahydro-1,3,5-triazine-2,6-dione.

16. Dione compound as claimed in claim 1 designated 1-cyclohexyl-3-isopropylideneamino-4-methylmercapto-tetrahydro-1,3,5-triazine-2,6-dione.

17. Dione compound as claimed in claim 1 designated 1-cyclohexyl-3-amino-4-methylmercapto-tetrahydro-1,3,5-triazine-2,6-dione.

18. Dione compound as claimed in claim 1 designated 1-isopropyl-3-amino-4-methylmercapto-tetrahydro-1,3,5-triazine-2,6-dione.

19. Dione compound as claimed in claim 1 wherein $R^1$ is branched alkyl of from 1 to 12 carbon atoms.

* * * * *